US012138639B2

(12) United States Patent
James et al.

(10) Patent No.: US 12,138,639 B2
(45) Date of Patent: Nov. 12, 2024

(54) SYSTEM, METHOD AND CONTROLLER FOR RECOVERY OF CONCENTRATED PARTICLES SUSPENDED IN FLUID

(71) Applicant: SCINOGY PRODUCTS PTY LTD, Mount Martha (AU)

(72) Inventors: David James, Mount Martha (AU); Stephen Wilson, Mount Martha (AU); Ian Fitzpatrick, Mount Martha (AU)

(73) Assignee: Scinogy Products Pty Ltd, Mount Martha (AU)

( * ) Notice: Subject to any disclaimer, the term of this patent is extended or adjusted under 35 U.S.C. 154(b) by 1057 days.

(21) Appl. No.: 16/963,466

(22) PCT Filed: Jan. 22, 2019

(86) PCT No.: PCT/AU2019/050036
§ 371 (c)(1),
(2) Date: Jul. 20, 2020

(87) PCT Pub. No.: WO2019/140491
PCT Pub. Date: Jul. 25, 2019

(65) Prior Publication Data
US 2021/0046489 A1 Feb. 18, 2021

(30) Foreign Application Priority Data

Jan. 22, 2018 (AU) .................. 2018900191
Oct. 19, 2018 (AU) .................. 2018903959

(51) Int. Cl.
*B04B 5/04* (2006.01)
*A61M 1/36* (2006.01)
(Continued)

(52) U.S. Cl.
CPC ......... *B04B 5/0442* (2013.01); *A61M 1/3693* (2013.01); *B01D 21/262* (2013.01);
(Continued)

(58) Field of Classification Search
CPC .............. B04B 5/0442; B04B 11/02; B04B 2005/0471; B04B 5/0407; A61M 1/3693;
(Continued)

(56) References Cited

U.S. PATENT DOCUMENTS 4,464,167 A    8/1984    Schoendorfer et al.
5,607,579 A    3/1997    Latham, Jr. et al.
(Continued)

FOREIGN PATENT DOCUMENTS

CN    1261815 A        2/2000
EP    0 885 619 A1    12/1998
(Continued)

OTHER PUBLICATIONS

Extended European Search Report dated Sep. 17, 2021 in European Application No. 19741073.1.
(Continued)

*Primary Examiner* — Walter D. Griffin
*Assistant Examiner* — Shuyi S. Liu
(74) *Attorney, Agent, or Firm* — Knobbe Martens Olson & Bear LLP

(57) ABSTRACT

Embodiments provide a fluid recovery system and method for use with concentrator systems for concentrating particles suspended in a fluid and where this suspension is recovered from a fluid stream drawn from the concentrator system. A controller is configured to control valve actuation to direct concentrate being drawn from the concentrator chamber through a recovery tube to a recovery reservoir based on fluid volume movement. The system can use a density sensor to detect density transitions in fluid in the fluid recovery tube to identify leading and trailing edges of a portion of concentrated particles in fluid suspension passing (Continued)

through the recovery tube and actuate recovery valves based on objectives for maximising particle recovery with minimal dilution.

21 Claims, 12 Drawing Sheets

(51) Int. Cl.
*B01D 21/26* (2006.01)
*B04B 11/02* (2006.01)
*G01N 15/06* (2024.01)
*G01N 15/075* (2024.01)

(52) U.S. Cl.
CPC .............. *B04B 11/02* (2013.01); *G01N 15/06* (2013.01); *A61M 2205/3306* (2013.01); *B04B 2005/0471* (2013.01); *G01N 15/075* (2024.01)

(58) Field of Classification Search
CPC ........ A61M 2205/3306; A61M 1/0281; A61M 1/0272; A61M 1/029; B01D 21/262; B01D 21/26; G01N 15/06; G01N 2015/0693; G01N 9/32; G01N 9/30; G01F 1/86
See application file for complete search history.

(56) References Cited

U.S. PATENT DOCUMENTS

| | | | | |
|---|---|---|---|---|
| 5,980,757 | A | | 11/1999 | Brown et al. |
| 5,980,760 | A | * | 11/1999 | Min .................... B01D 21/262 210/85 |
| 2004/0058794 | A1 | | 3/2004 | Dolecek et al. |

FOREIGN PATENT DOCUMENTS

| | | | |
|---|---|---|---|
| WO | WO 99/01197 | A1 | 1/1999 |
| WO | WO 01/03798 | A1 | 1/2001 |
| WO | WO 2008/021633 | A2 | 2/2008 |
| WO | WO 2017/062176 | A1 | 4/2017 |

OTHER PUBLICATIONS

Examination Report dated Jan. 18, 2022 in Indian Application No. 202017031865.

International Search Report mailed Mar. 4, 2019 in International Application No. PCT/AU2019/050036, in 6 pages.

* cited by examiner

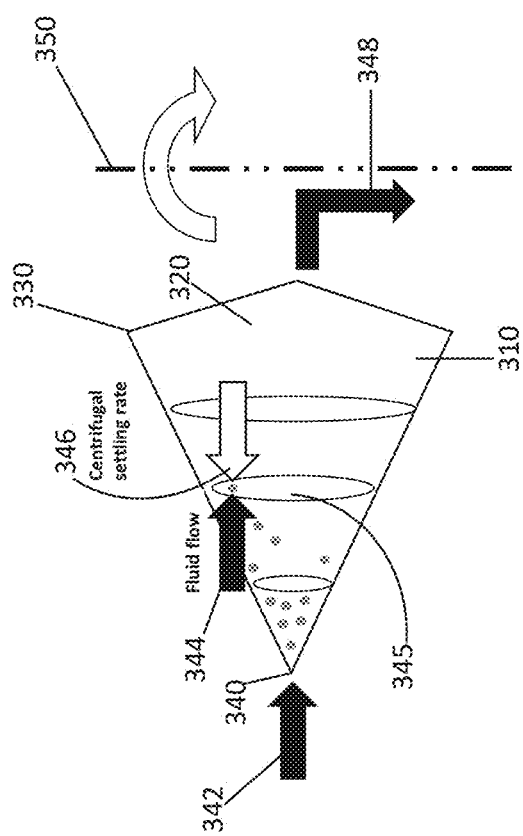

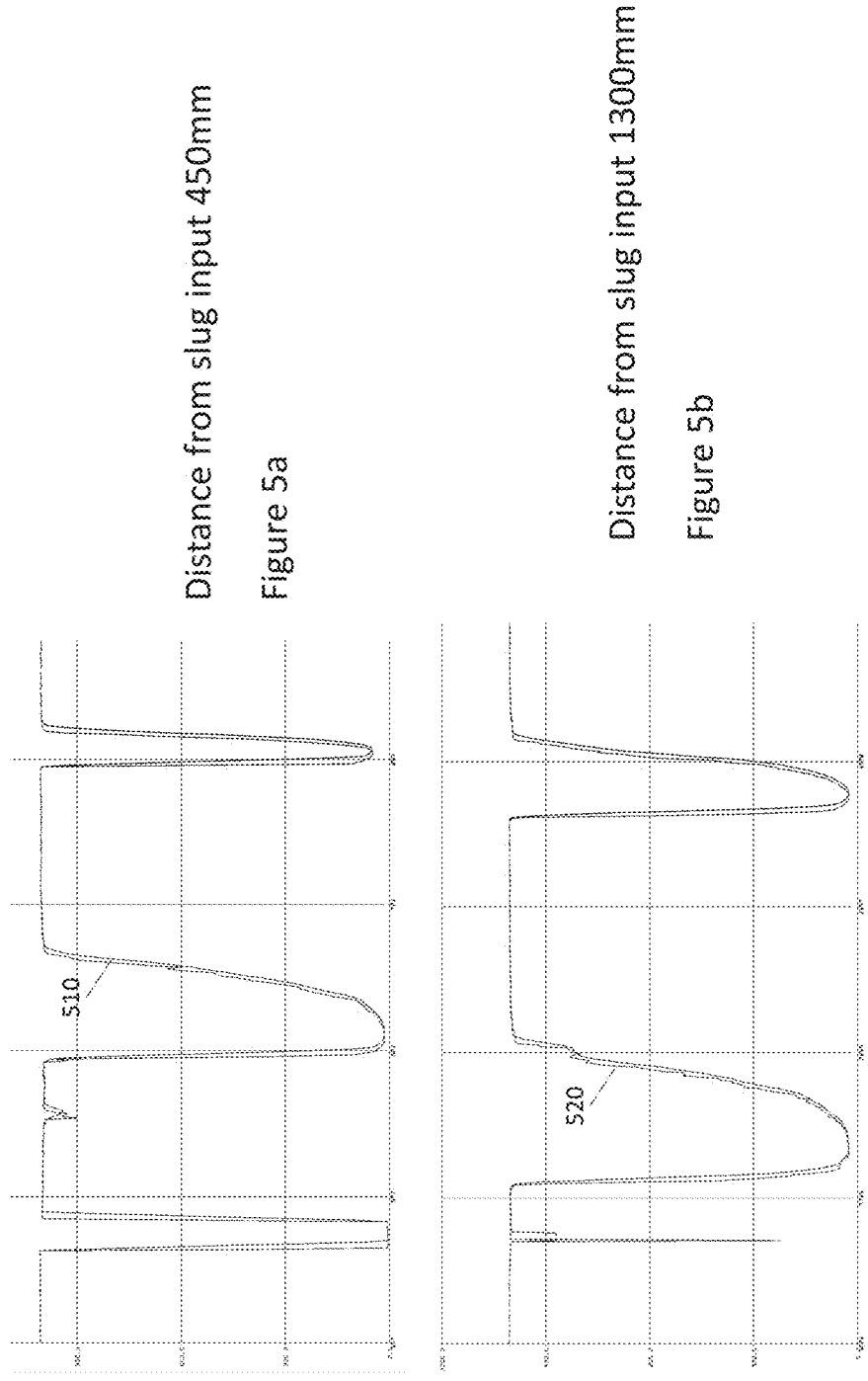

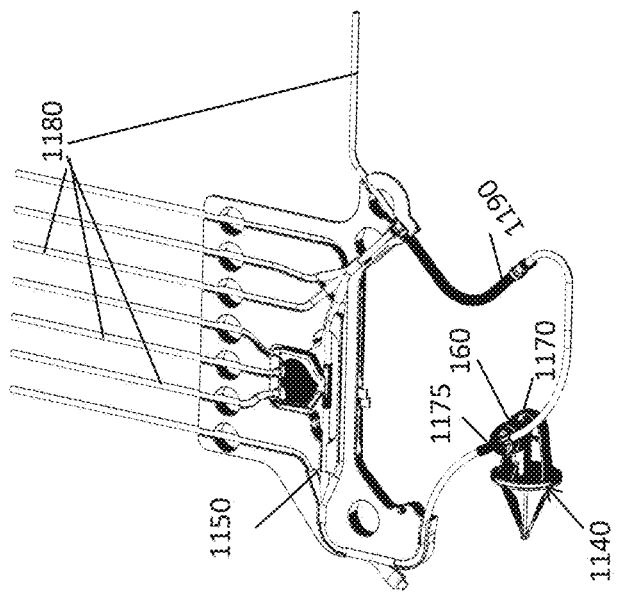
Figure 6c
Single Use Kit 1205
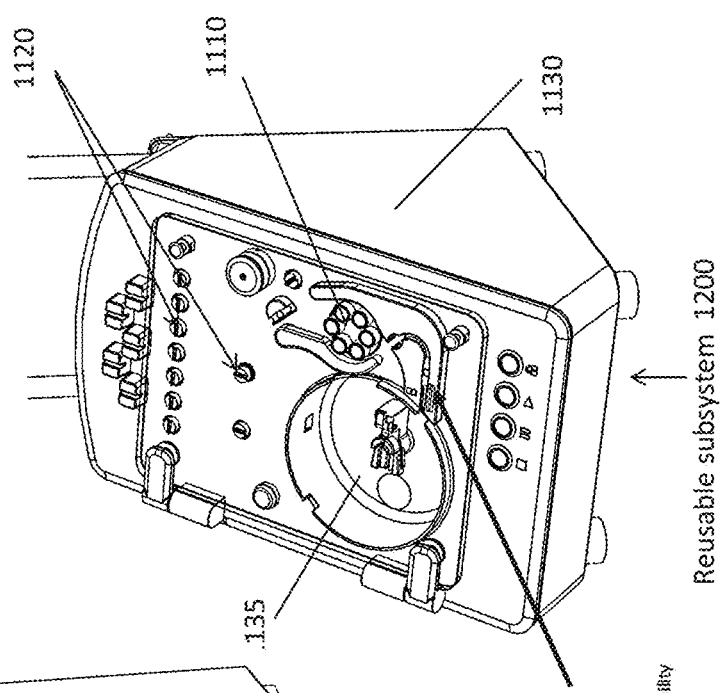
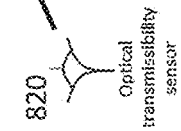
Figure 6b
Reusable subsystem 1200
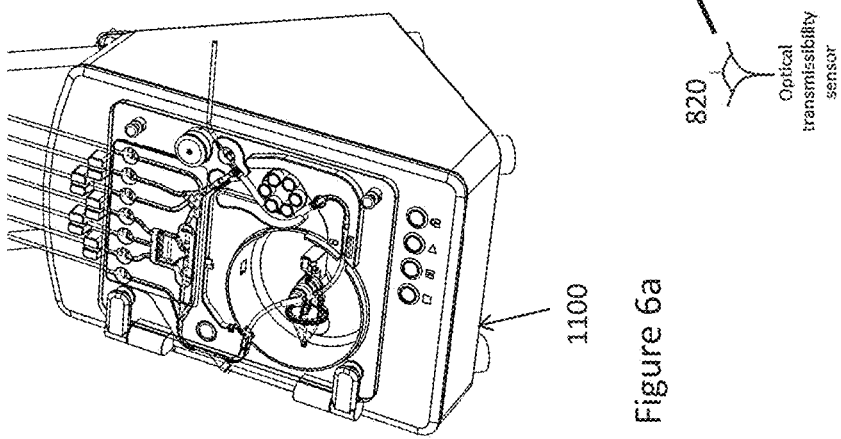
Figure 6a

Figure 10

SYSTEM, METHOD AND CONTROLLER FOR RECOVERY OF CONCENTRATED PARTICLES SUSPENDED IN FLUID

CROSS REFERENCE TO RELATED APPLICATIONS

The present application is a U.S. national phase application under 35 U.S.C. § 371 of International Application No. PCT/AU2019/050036, filed on Jan. 22, 2019 and published as WO 2019/140491 A1 on Jul. 25, 2019, which claims priority to AU Application Nos. 2018900191, filed on Jan. 22, 2018, and 2018903959, filed on Oct. 19, 2018. The content of each of these applications is incorporated herein by reference in its entirety.

TECHNICAL FIELD

The technical field of the invention is a system, method and controller for recovery of fluid from an apparatus used for concentrating particles in a fluid suspension, an example of an application for the system is for operation with a counter flow centrifuge apparatus for biological and other small particle separation applications.

BACKGROUND

Regenerative medicine and advanced cell therapies are emerging medical therapeutic technologies that build on manipulation of live, human derived cells to create constructs, deliver immunogenic responses or stimulate repair responses in the patient body. While some of these techniques can deliver many doses to multiple patients from a single source of cell (allogeneic products) there is growing recognition that processing and delivering cells derived from the patient or matched donor is safe and efficacious. To produce patient or matched donor specific cell products (autologous products) typically requires small batch processing.

Traditional centrifugation techniques require a vessel containing the product to be manually transferred into and out of the centrifugation device. Traditional centrifuge systems cause cells to sediment in the end of the vessel and form a pellet. Accessing the vessel to add or remove product requires opening the vessel as an open process step or coupling and disconnecting it to an aseptic path.

Counter flow centrifugation with integrated fluid flow through the rotation system can be used to avoid these interactions. Counter flow centrifugation is a technique whereby the settling rate of particles in a fluid under centrifugal acceleration is counteracted by a flow of the supporting media. The particles are thereby suspended in a fluidized bed. In the case of cell therapies the fluidised bed will be a concentration of cells suspended in the media fluid. Cells are recovered as a concentration of cells suspended in fluid rather than a pellet as is created using traditional centrifugation.

Counter flow centrifugation is so gentle that cells can be cultured, expanding in the fluidised bed state. Cell aggregation can be dramatically reduced relative to traditional sedimentation. Further this technique enables separation of dead cells from live cells due to different density and morphology characteristics making counter flow centrifugation the only currently available technology for increasing the viability of a cell population.

Delivering a fluid flow radially inwards to cells or particles under centrifugal acceleration creates the counter flow situation. The centrifugal acceleration experienced by each particle is proportional to the radial distance of that particle from the centre of rotation. To create a bed of fluidized particles the counteracting flow rate needs to be adjusted for each radius of rotation. This is achieved by shaping the chamber, commonly as a cone with the tip of the cone pointing radially outwards. The counter fluid flow is input through the cone tip. The fluid flow enters the tip of the cone at a relatively high velocity and the velocity of the input fluid flow progressively reduces as it progresses radially inwards due to the increasing cross section of the cone. The concentrated particles suspended in the media fluid are recovered by reversing the fluid flow and drawing the concentrated particle suspension fluid from the tip of the conical separation chamber. The volume of the concentrated cell suspension in the fluidised bed will depend on the number of cells and fluidised bed density, and this volume can be very small.

Manufacturing complex medical products as a batch for each patient is creating demand for devices that can manipulate cell products within single-use functionally closed systems. Counter flow centrifugation has many benefits and is currently used in a number of commercially available dedicated functionally closed systems. However, commercially available counter flow centrifuge systems typically operate using larger volumes than is desirable for autologous cell therapies. Recovery of very small volumes of concentrated fluids is required to enable practical commercial realisation of autologous cell therapies.

There is a need for equipment that can be reliably utilised for single use small batch processing and accurate low volume recovery to enable production of such patient specific cell products.

Autologous products can comprise very small quantities of input and output cell product. Successful processing requires methods that can deal with small cell populations with minimal loss and the ability to complete all processing with the minimum number of manipulations. The final steps of a cell product protocol typically require a knowledge of the cell population to direct the final formulation steps ready for fill and finish. The volumes of reagents and final product can be in the 1 to 2 ml range demanding close attention to fluid volume control. Processing patient specific products for multiple patients is further promoted by parallel processing of batches in a common low-grade space through the use of functionally closed processing methods that contain the product inside bags and tubes to avoid exposure to the external environment. Products that require aseptic manipulation benefit by processing in single use vessels. The key benefit is pre-qualification of the processing system sterility prior to commencement of the batch as part of the single use product supply chain. This avoids the cost and delays associated with in-place sterilisation and verification methods.

This invention describes equipment, sensors, control strategies and processing vessels that facilitate manipulation of small cell populations that have been concentrated as a fluidised bed within a single use counter flow centrifugation system.

SUMMARY OF THE INVENTION

A first aspect provides a fluid recovery system configured to operatively engage with a concentrator apparatus comprising a concentrating chamber having a first fluid path and a second fluid path connected in line with a pumping mechanism, whereby to recover concentrated fluid from the concentrating chamber fluid enters the concentrating chamber via the first fluid path as fluid exits the concentrating chamber via the second fluid path to a fluid recovery tube, and a recovery valve assembly and valve actuator configured to switch flow of fluid from the fluid recovery tube one of two or more output fluid tubes, at least one fluid output tube providing a fluid capture path and at least one fluid output tube providing a non-capture path;
the fluid recovery system comprising:
 a density sensor configured to detect density of fluid in the recovery tube preceding the recovery valve assembly when operatively engaged with the concentrator apparatus; and
 a controller configured to:
  monitor operation of the fluid pumping mechanism to determine dynamic fluid volume movement of fluid in the fluid recovery tube,
  monitor the density sensor to identify:
   a first density transition in fluid in the fluid recovery tube from a first density to second density, the second density being higher than the first density, the density transition being indicative of a leading edge of a portion of concentrated particles in the fluid passing through the recovery tube; and
   a second density transition from the second density to a third density, the third density being lower than the second density, the density transition being indicative of a trailing edge of a portion of concentrated particles in the fluid passing through the recovery tube;

and determine based on a fluidic volume between the concentrating chamber outlet and recovery valve assembly a first control event for switching fluid flow in the fluid recovery tube to the fluid capture path;

determine, based on detection of the first density transition, the second density transition and dynamic fluid volume movement, a volume of suspension containing target material for recovery, determine a second control event for switching fluid flow in the fluid recovery tube from the fluid capture path to a non-capture path to capture the volume of suspension containing target material for recovery; and control operation of the valve actuator in accordance with the first control event to switch between a non-capture path and a fluid capture path, and in accordance with the second control event to switch fluid flow between the fluid capture path and a non-capture path.

In some embodiments the controller is further configured to operate the pumping mechanism to control the dynamic fluid volume movement. In some embodiments the pumping mechanism is a peristaltic pump and the controller is configured to monitor the dynamic fluid volume movement based on and monitoring rotary position of the pump and/or calibration of the pump tube. In some embodiments the controller is further configured to control dynamic fluid volume movement based on knowledge of the rotary pump position. In some embodiments the controller is further configured to control dynamic fluid volume movement based on knowledge of the rotary position of pump occlusion members.

In some embodiments the controller is configured to determine the first control event for operation of the valve actuator based on a calculated volume preceding a collection start trigger relative to the leading edge of the particle concentrate in the fluid and the volume of fluid in the recovery tube between the density sensor and valve assembly. In an embodiment the collection start trigger is a collection threshold density. In an embodiment where the density sensor is an optical density sensor the density is determined based on transmissibility if the fluid in the tube. The threshold density being a transmissibility relative to a "clear fluid in tube" transmissibility baseline and the controller is configured to accumulate the baseline transmissibility that facilitates the transmissibility-based threshold levels to be compared as ratios without absolute calibration of the sensor.

The controller can be configured to determine the second control event for operation of the valve actuator based on a calculated volume preceding a "collection stop" trigger relative to the trailing edge of the concentrated fluid and the volume of fluid in the recovery tube between the density sensor and the valve assembly. In an example the collection stop trigger is a concentrate dilution threshold density relative to a baseline density (or transmissibility for optical sensor embodiments) and the controller is configured to analyse the second density transition to determine the second control event for operation of the valve actuator based on the concentrate dilution threshold density. In some embodiments selection of the concentrate dilution threshold can maximise the cell density delivered to the fluid capture path.

In some embodiments the controller is further configured to determine a first control event based on volume of fluid between the concentrating chamber and valve assembly and dynamic fluid volume movement, to cause actuation of the valve actuator to switch to a collection path based on volume in the absence of a density sensor-based collection trigger.

The controller can be further configured to determine a second control event based on a specified delivery volume in the absence of a density sensor-based collection trigger.

A second aspect provides a concentrator apparatus comprising:

a pumping mechanism;

a concentrating chamber having a first fluid path and a second fluid path connected in line with the pumping mechanism to introduce fluid to the concentrating chamber, whereby to recover concentrated fluid from the concentrating chamber fluid enters the concentrating chamber via the first fluid path as fluid exits the concentrating chamber via the second fluid path;

a fluid recovery tube connected to the second fluid path of the concentrating chamber;

a recovery valve assembly and valve actuator configured to switch flow of fluid from the fluid recovery tube one of two or more output fluid tubes, at least one fluid output tube providing a fluid capture path and at least one fluid output tube providing a non-capture path;

a density sensor configured to be positioned to detect density of fluid in the recovery tube preceding the recovery valve assembly, when operatively engaged with the concentrator apparatus; and a controller configured to:

control operation of the fluid pumping mechanism to control dynamic fluid volume movement of fluid in the fluid recovery tube, monitor the density sensor to identify:

a first density transition in fluid in the fluid recovery tube from a first density to second density, the second density being higher than the first density, the density transition being indicative of a leading edge of a portion of concentrated fluid passing through the recovery tube; and a second density transition from the second density to a third density, the third density being lower than the second density, the density transition being indicative of a trailing edge of a portion of concentrated fluid passing through the recovery tube;
and
determine based on a fluidic volume between the concentrating chamber outlet and recovery valve assembly a first control event for switching fluid flow in the fluid recovery tube to the fluid capture path;
determine based on detection of the first density transition, the second density transition and dynamic fluid volume movement, a volume of suspension containing target material for recovery;
determine a second control event for switching fluid flow in the fluid recovery tube from the fluid capture path to a non-capture path to capture the volume of suspension continuing target material for recovery; and control operation of the valve actuator in accordance with the first control event to switch between a non-capture path and a fluid capture path, and in accordance with the second control event to switch fluid flow between the fluid capture path and a non-capture path.

In an embodiment the concentrator apparatus is a counter flow centrifuge and the controller is further configured to control concentrating chamber rotation and the pumping mechanism to:

during a separation operation phase cause fluid flow in a counter flow direction to cause fluid to enter concentrating chamber via the second fluid path whereby centrifugal force due to rotation of the concentrating chamber and the counter fluid flow cause concentration of particles in the fluid into a fluidised bed to provide the concentrated fluid, and during a recovery operation phase cause fluid flow in a recovery direction to cause fluid to enter the chamber via the first fluid path as fluid is drawn from the concentrating chamber via the second fluid path, whereby the fluid flow and centrifugal force due to rotation of the concentrating chamber cause the fluidised bed of concentrated fluid to move to the second fluid path and be drawn from the concentrating chamber through the fluid recovery tube.

In an embodiment of the concentrator apparatus the controller is configured to slow operation of the pumping mechanism and chamber rotation in a time coordinated manner sustaining the stability of the fluidised bed counter flow conditions prior to the recovery operation phase.

In an embodiment the counter flow centrifuge is a compact counter flow centrifuge system comprising:

a reusable subsystem; and a single use, replaceable subsystem, the reusable subsystem comprising:

a rotating motor head;

a peristaltic pump;

a valve assembly; and case housing the rotating head, peristaltic pump, and valve operation assembly, and the single use, replaceable subsystem comprising:

a separation chamber configured for low fluid volume and small radius rotation, comprising a substantially conical fluid enclosure portion connected to a neck portion, and having a dip tube extending centrally through the conical fluid enclosure from the conical tip through the neck to provide a fluid path to the tip of the conical fluid enclosure, the neck portion further comprising an elution fluid path;

a fluid delivery manifold comprising a first fluid port and a second fluid port configured for fluid communication with the separation chamber, a plurality of fluid paths configured for connection to external fluid supply components for delivery of fluid to or from the first fluid port and the second fluid port at least one of the fluid paths being configured for engagement with the valve assembly whereby fluid paths can be selectively opened or closed by operation of the valve assembly, and a pump engagement portion configured to enable operable engagement between the peristaltic pump and fluid paths to cause fluid flow within the manifold by operation of the peristaltic pump; and a rotary coupling connecting the neck portion of the separation chamber to the fluid delivery manifold and providing a first fluid communication path between the dip tube and the first fluid port and a second fluid communication path between the elution fluid path and the second fluid port, the rotary coupling being configured to allow rotation of the separation chamber about a rotational axis relative to the fluid delivery manifold while the fluid delivery manifold is held in a fixed position by the case;

the neck portion being further configured to engage with the rotating motor head to cause rotation of the separation chamber about the rotational axis, the single use replaceable subsystem providing a closed environment for execution of counter flow centrifugation processes.

In this embodiment of the concentrator apparatus the pump, density sensor and valve assembly can be arranged to provide a short fluid path length for a recovery path from the separation chamber through the manifold past the density sensor and a pump engagement portion to an output.

The controller can be configured to monitor the dynamic fluid volume movement based on and monitoring rotary position of the peristaltic pump and/or calibration of the pump tube. The controller can be further configured to control dynamic fluid volume movement based on knowledge of the rotary pump position. The controller can be further configured to control dynamic fluid volume movement based on knowledge of the rotary position of pump occlusion members.

In an embodiment the controller is configured to determine the first control event for operation of the valve actuator based on a known volume between the dip tube in the concentrator apparatus and valve assembly. The collection volume start trigger can be a density threshold relative to a baseline optical density determined at the commencement of the event before concentrated particles are present in the recovery tube. The collection volume can be determined from a second optical density threshold where the transmissibility returns to the baseline optical density. The threshold can be specified as a percentage of the baseline value to preclude sensitivity to absolute calibration of the optical density sensor. In an embodiment the controller determines a concentrate delivery volume from the observed volumetric flow between the optical density threshold events.

In an embodiment the controller can be configured to determine the second control event for operation of the valve actuator based on the first control event with addition of the concentrate delivery volume. It must be understood that the second density threshold may not have occurred when the first control event occurs. In an embodiment the controller can anticipate a second threshold event since a first threshold event has occurred before the first control event. In this case the second optical density threshold event will define the concentrate delivery volume that shall be delivered after the first control event. The collection threshold density and concentrate dilution threshold density can be selected to maximise concentration of the fluid delivered to the collection path.

In an embodiment the controller is further configured to determine a first control event based on volume of fluid between the concentrating chamber and valve assembly and dynamic fluid volume movement, to cause actuation of the valve actuator to switch to a collection path based on volume in the absence of a density sensor-based collection trigger. The controller can be further configured to determine a second control event based on a specified volume in the absence of a density sensor-based collection trigger.

Another aspect provides a concentrated fluid recovery method implemented in a fluid recovery system of a concentrator apparatus comprising a pumping mechanism, concentrating chamber having a first fluid path and a second fluid path connected in line with the pumping mechanism, whereby to recover concentrated fluid from the concentrating chamber fluid enters the concentrating chamber via the first fluid path as fluid exits the concentrating chamber via the second fluid path to a fluid recovery tube, and a recovery valve assembly and valve actuator configured to switch flow of fluid from the fluid recovery tube one of two or more output fluid tubes, at least one fluid output tube providing a fluid capture path and at least one fluid output tube providing a non-capture path; a density sensor configured to be positioned to detect density of fluid in the recovery tube a fixed distance along the fluid recovery tube preceding the recovery valve assembly, when operatively engaged with the concentrator apparatus; and a controller;

the method comprising the steps of:
  monitoring by the controller operation of the fluid pumping mechanism to determine dynamic fluid volume movement of fluid in the fluid recovery tube,
  monitoring by the controller using the density sensor the density of fluid flowing in the recovery tube;
  identifying a first density transition in fluid in the fluid recovery tube from a first density to second density, the second density being higher than the first density, the density transition being indicative of a leading edge of a portion of concentrated fluid passing through the recovery tube;
  determining by the controller based on detection of the first density transition, dynamic fluid volume movement, and distance between the density sensor and recovery valve assembly a first control event for switching fluid flow in the fluid recovery tube to the fluid capture path;
  identifying a second density transition from the second density to a third density, the third density being lower than the second density, the density transition being indicative of a trailing edge of a portion of concentrated fluid passing through the recovery tube;
  determining based on detection of the second density transition, dynamic fluid volume movement, and distance between the density sensor and recovery valve assembly a second control event for switching fluid flow in the fluid recovery tube from the fluid capture path to a non-capture path; and
  controlling operation of the valve actuator in accordance with the first control event to switch between a non-capture path and a fluid capture path, and
  controlling operation of the valve actuator in accordance with the second control event to switch fluid flow between the fluid capture path and a non-capture path.

The method can further include the step of controlling pump operation to thereby control dynamic fluid volume movement.

In an embodiment of the method determining the first control event for operation of the valve actuator is based on a calculated volume preceding a collection start trigger relative to the leading edge of the concentrated fluid and the volume of fluid in the recovery tube between the density sensor and valve assembly. In an embodiment of the method the collection start trigger is a collection threshold density relative to a baseline density.

In an embodiment of the method determining the second control event for operation of the valve actuator is based on a calculated volume preceding a collection stop trigger relative to the trailing edge of the concentrated fluid. In an embodiment of the method the collection stop trigger is a dilution threshold density relative to a baseline density, the method further comprises the steps of analysing the second density transition and determining the second control event for operation of the valve actuator based on the collection stop trigger. In an embodiment of the method the collection threshold density and dilution threshold density are selected to minimise dilution of the output product by fluid trailing the concentrate in the tube.

An embodiment of the method further comprises the step of determining a first control event based on volume of fluid between the concentrating chamber and valve assembly and dynamic fluid volume movement, to cause actuation of the valve actuator to switch to a collection path based on volume in the absence of a density sensor-based collection trigger. An embodiment further comprises the step of determining a second control event based on a specified capture volume in the absence of a density sensor-based collection trigger.

In an embodiment of the method where the concentrator apparatus is a counter flow centrifuge, the method further comprises the step of slowing operation of the pumping mechanism and chamber rotation in a coordinated action sustaining the stability of the fluidised bed counter flow conditions prior to the recovery operation phase.

BRIEF DESCRIPTION OF THE DRAWINGS

An embodiment, incorporating all aspects of the invention, will now be described by way of example only with reference to the accompanying drawings in which:

FIG. 3 illustrates the fundamental concepts involved in a counter flow centrifugation process;

FIGS. 5a and 5b show examples of optical density measurements for slugs of particle concentrate of the same volume taken at varying distances along the tube from the chamber outlet to demonstrate the draw out effects on the slug, caused by laminar flow, increase with tube length;

FIGS. 6a-c is an example of an embodiment of a compact counter flow centrifuge instrument and associated single use kit incorporating an embodiment of the fluid recovery system, showing the assembled instrument in FIG. 6a, the reusable subsystem in FIG. 6b and single use kit in FIG. 6c;

FIG. 10 show an example of settings for an optical density sensor; and

DETAILED DESCRIPTION

Figure 1:
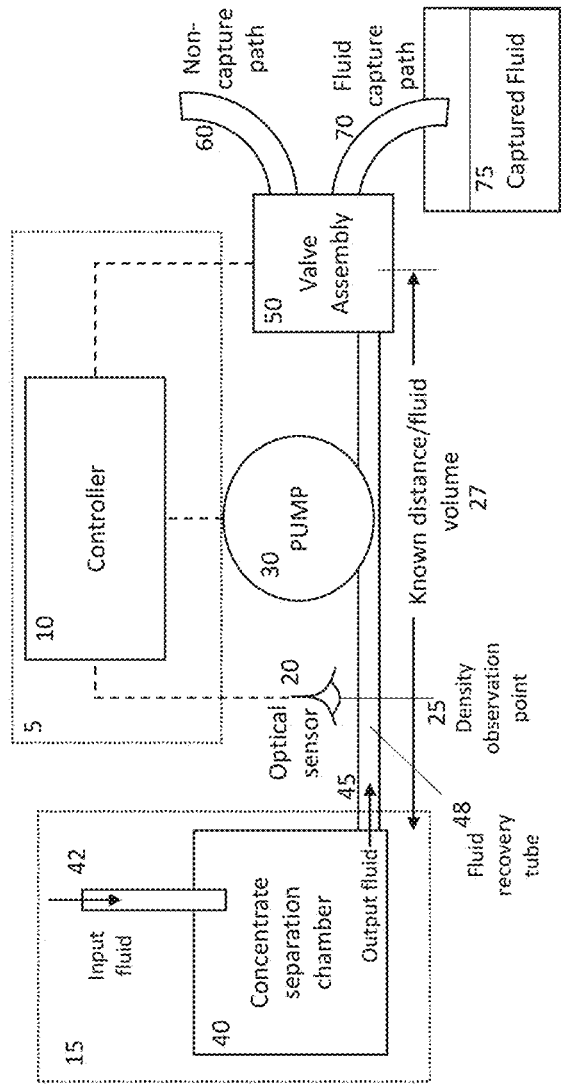
FIG. 1 is a representative block diagram of an embodiment of a fluid recovery system.

Embodiments provide a fluid recovery system and method for use with concentrator systems for concentrating particles suspended in a fluid and where this suspension is recovered from a fluid stream drawn from the concentrator system. For example, the Embodiment of the fluid recovery system comprises a density sensor and a controller configured to operatively engage with a concentrator apparatus. The block diagram of FIG. 1 represents a fluid recovery system 5 comprising a controller 10 and density sensor 20 operatively engaged with a concentrator apparatus 15, configured for concentrating particles suspended in fluid. The concentrator apparatus comprises a concentrating chamber 40 having a first fluid path 42 and a second fluid path 45 connected in line with a pumping mechanism 30. In such systems, to recover concentrated fluid from the concentrating chamber, fluid enters the concentrating chamber 40 via the first fluid path 42 as fluid exits the concentrating chamber via the second fluid path 45 to a fluid recovery tube 48.

Operation of the pumping mechanism 30 causes the fluid flow through the system, i.e. from the first fluid path 42, through the chamber 40, through the second fluid path 45 and recovery tube 48. It should be appreciated that a pumping mechanism may be controlled to control a pump output fluid flow rate, for example ml/s. However, the fluid velocity through various segments of the system will vary based on system geometry, for example fluid will flow faster in a small tube compared with flow rate through a wider chamber. A conical separation chamber of a counter flow centrifuge exhibits different flow velocity through the chamber due to the changing chamber diameter. It should be appreciated that, in a sealed fluid flow path of a system, a pump flow rate will correspond to the volume of fluid moved through the system, even though various parts of the system may experience different velocity due to system geometry. Changes in pump speed and therefore flow rate causes corresponding change in fluid volume moved. In the present description the term dynamic fluid volume movement is used to refer to an instantaneous value of such changeable movement in fluid volume.

A recovery valve assembly 50 and valve actuator (not shown) can be configured to switch flow of fluid from the fluid recovery tube 45 one of two or more output fluid tubes, at least one fluid output tube 70 providing a fluid capture path and at least one fluid output tube 60 providing a non-capture path. When the fluid recovery system is operatively engaged with the concentrator apparatus 15, the density sensor 20 is configured to detect density of fluid in the recovery tube 48 preceding the recovery valve assembly 50. There is a known volume of fluid 27 between the chamber output 48 and the output valve assembly 50. It should be appreciated that the density sensor can be positioned anywhere within the fluid recovery path. The density sensor will provide an indication of density of concentrated particles in the fluid passing through the recovery tube. The actual position in the fluid path is not important. The controller will determine a concentrate volume to recover based on the optical density and the dynamic fluid volume. The fluid recovery can be based on detection of threshold concentrations of particles in suspension between threshold density settings.

The controller 10 is configured to monitor operation of the fluid pumping mechanism 30 to determine dynamic fluid movement volume in the fluid recovery tube, and monitor the density sensor. The controller is configured to identify, from the density sensor output, a first density transition in fluid in the fluid recovery tube from a first density to second density, the second density being higher than the first density, this density transition being indicative of a leading edge of a portion of concentrated particles in fluid suspension passing through the recovery tube 48. The controller is also configured to identify from the density sensor output a second density transition from the second density to a third density, the third density being lower than the sending density, this density transition being indicative of a trailing edge of the concentrated fluid suspension passing through the recovery tube 48.

Figures 2A, 2B:
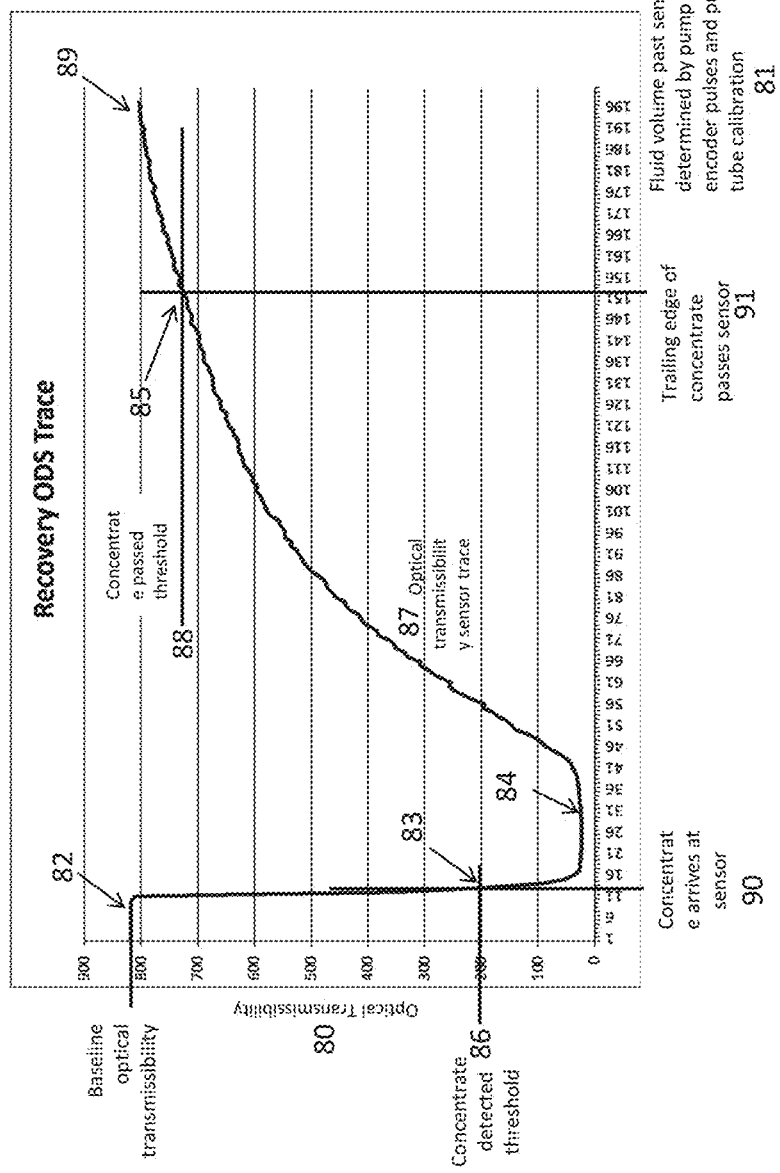
FIG. 2a is an example of an optical density sensor output graph, graphing the change in light transmissibility across a fluid recovery tube over time as a concentrated suspension of particles passes the optical sensor.
FIG. 2b is an example of a controller user interface for setting start collection and end collection threshold triggers specified as a percentage of a baseline reading.

In an embodiment the density sensor 20 can be an optical density sensor, detecting change in light transmissibility of fluid as the suspension passes the density sensor. An example of a transmissibility graph is shown in FIG. 2a, showing an example of an optical density sensor output, graphing the change in light transmissibility 80 across a fluid recovery tube against the fluid volume that has passed the sensor 81 as a slug of concentrated particles in suspension passes the optical sensor. As shown in FIG. 2a, initially the optical transmissibility is high 82, as would be expected for a substantially clear media fluid preceding the slug. The first density transition 83 is relatively steep, indicating a rapid change from high 82 to low 84 transmissibility as the concentrate arrives at the density sensor 90. A second density transition 85 occurs as the trailing edge of the slug passes the sensor 91, showing a transition 85 from low transmissibility 84 returning to high transmissibility 89 of the particle free fluid media. The system can be configured to identify a concentrate detection threshold 86 and a concentrate passed threshold 88 based on transmissibility of fluid in the recovery tube relative to the clear fluid transmissibility 82 observed at commencement of the controlled action.

By monitoring the density threshold transition events concurrently with the dynamic fluid volume, the controller determines a fluid volume that represents the concentrate as determined by the threshold settings.

In parallel to determination of the density-based concentrate volume detection, the controller 10 monitors the dynamic fluid volume in the fluid recovery tube 48 to determine when a known fluid volume 27 between the chamber outlet and the valve assembly 50 has been completed. This event triggers switching the fluid flow from the non-capture path to the capture path. At that time the controller commences monitoring the dynamic fluid volume to determine if the density sensor determined volume has been delivered or some other event, such as a pre-set delivery volume has been completed. When this occurs, the controller switches the fluid path to the Non-capture path 60 from the fluid capture path 70.

Embodiments of the fluid recovery system and method are configured to detect the leading and trailing edges of the concentrated particle suspension in the fluid stream being recovered from the concentrating chamber. In an embodiment the density sensor 20 is an optical density sensor. The optical density sensor measures the light transmissibility of the fluid flowing in the recovery tube, for example as shown in FIG. 2a. The fluid flowing through the recovery tube will typically be media fluid substantially clear of particles preceding and succeeding the concentration of particles suspended in media fluid. For example, a fluidised bed of particles can be drawn out through a recovery tube by the flow of media from a separation chamber as a "slug" of particles suspended at relatively high concentration compared with the substantially particle free media fluid, which flows through the tube ahead of the suspension "slug" and following the suspension "slug". The light permeability of the concentration of particles suspended in the media fluid is expected to be different than that of the media fluid alone or with relatively low concentrations of particles, for example lower light transmissibility through the higher particle concentration suspension than through the substantially particle free leading and following media fluid. Light permeability can also be referred to an opaqueness or transmissibility. A concentration of particles suspended in a fluidised bed will typically appear more opaque than the surrounding fluid.

The first density transition 83 may be identified from a change in light transmissibility, sensed by the optical sensor. In an example this may be a decrease in light permeability in the fluid flowing though the recovery tube.

It is common for live cell protocols to seek a target cell concentration (cells/ml) in the output product. When cells are rare and precious it is particularly important to recover the cells, you have in the smallest practical volume to enable dilution to the target final formulation volume rather than additional concentration steps.

One should also understand that the concentrating chamber is unlikely to be comprehensively full of cells. Different protocols and batches will result in different cell populations and therefore different volumes required to be recovered. In one embodiment deployed in a counter flow centrifugation device cells accumulate in the concentrating chamber from the tip building the fluidised bed progressively. This allows those cells that are available to be recovered as a slug of concentrate. When operating conditions and suspension media are consistent, then the volume of the concentrate slug is representative of the number of cells that have been concentrated.

Embodiments of the present fluid recovery system include a density sensor across the fluid recovery path. In an embodiment this is an optical sensor which observes the transmissibility of light through the single use tubing forming the fluid recovery path.

In another embodiment change in density may be detected as a change in colour. In another embodiment change in density may be detected as a change in absorption at specific photon wavelengths. In another embodiment change in density may be detected as a change in frequency spectrum transmissibility through the fluid. In another embodiment the density sensor 20 may be a magnetic susceptibility sensor, configured to detect paramagnetic particles concentrated in a fluid suspension. In another embodiment density may be observed as intensity of photon emissions from the particles.

In an optical transmissibility embodiment, the optical transmissibility drops quickly when the cell concentrate "slug" initially moves past the optical density sensor as shown in FIG. 2a. As the last of the concentrate slug moves from the chamber past the sensor there is a recovery of the transmissibility observed by the sensor proportional to the reducing cell concentration in front of it, referred to herein as the trailing edge 85 of the slug.

In an embodiment the controller uses knowledge of a fixed volume between the concentrating chamber outlet 48 and the valve assembly 50. In alternative embodiments the controller uses knowledge of the position of the density sensor being a fixed distance from the valve assembly, enabling the volume of the tube between the optical sensor and the valve assembly to be known. This fixed volume may be predetermined or may be calculated by the system controller based on known equipment geometry (distance between the sensor and valve) and tube inner diameter based on a tube specification where different tubes may be used. For example, a user may input into the controller data to define disposable kit parts (i.e. selection of disposable kit of parts from a pick list or menu) which include the tubes, the corresponding tube specifications can be used by the controller to calculate the volume.

Through correlation of dynamic fluid volume movement through monitoring pump action and detection of the first and second density transitions the controller can determine a volume of the concentrate that traversed the sensor.

Through correlation of dynamic fluid volume movement through monitoring pump action and knowledge of the fluid volume between the concentrate separation chamber output 48 and the valve assembly 50, (refer FIG. 4 item 250) the controller 10 can coordinate the point where the valve assembly actuates to transfer flow from the non-capture path 60 to the fluid capture path 75.

The dynamic fluid volume where the first threshold 90 occurs is generally very predictable. This enables the first control event to be conducted independent of the density-based sensor events.

Figure 2D:
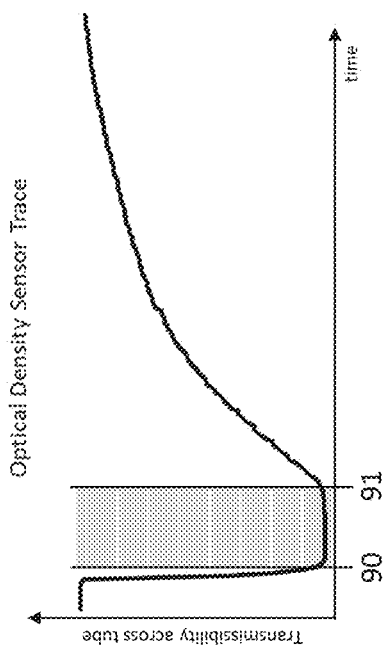
FIG. 2d illustrates a concentrate density trace, showing transmissibility of fluid in the recovery tube (indicating density of concentrated particles in the fluid) over time.

A further embodiment of the control design is to adjust opening of the delivery valve by the observed dynamic fluid volume for the concentrate to be maximised. By applying knowledge of the volume between the sensor and the cone tip (FIG. 4 item 260) the dynamic fluid volume where event 90 (FIG. 2a) occurs can direct the first control event. Through this means and further analysis of the concentrate density profile the control can direct the first control event to occur when maximum concentration product is presented to the delivery valve as illustrated in FIG. 2d.

A target delivery volume is determined by the density monitoring tool and through alternative definition means in the control such as a user defined pre-set, or through stored information from preceding process actions.

Through correlation of dynamic fluid volume movement through monitoring pump action and a target volume to be delivered the controller can coordinate the point where the valve assembly 50 will actuate from the fluid capture path 75 to the fluid non-capture path 60. For example, the valve actuation can be coordinated with the slug arriving at the valve to minimise dilution by leading and trailing fluid. Adjustment of the thresholds that drive the density transition detections enables maximum particle concentration recovery at the cost of trailing particles. Alternative adjustments of the trailing threshold can be set to minimise particle loss by including the trailing particles.

Embodiments of the fluid recovery system can be used with any concentrator apparatus for recovering concentrated particles suspended in fluid. Embodiments can be particularly advantageous for use with low volume concentrator apparatus. For example, some medical technologies recovery volumes for suspensions may be below 5 ml. Some cell therapy application examples may have desired recovery volumes below 1 ml if there are very few cells to recover.

One value criterion of any cell concentration step is how small a volume can the cells be recovered in. The concentrate recovery process objective is therefore to transfer only that volume of fluid containing the target cells past a concentrate recovery valve.

Based on physical volumes of the tubing coupling the concentrating chamber to the outlet valve the controller can predict arrival of the leading edge 83 of the concentrate at the valve assembly and when to operate the valve to divert the fluid flow to a recovery path.

The second event to operate the valve assembly to cease recovery of the cell suspension can be based on a pre-specified, fixed volume delivery, or a volume that is determined through monitoring the density transitions. It must be appreciated that the volume determined from the density transitions may not be fully defined when the first event occurs. Recognition that the first density threshold event has been identified can be used to direct the control system to deploy the density-based volume control rather than a "fallback" volume pre-set.

The second density transition that defines the density-based volume can also be dynamically determined even though the valve has already started delivering output to the fluid capture path 70.

Figure 2E:
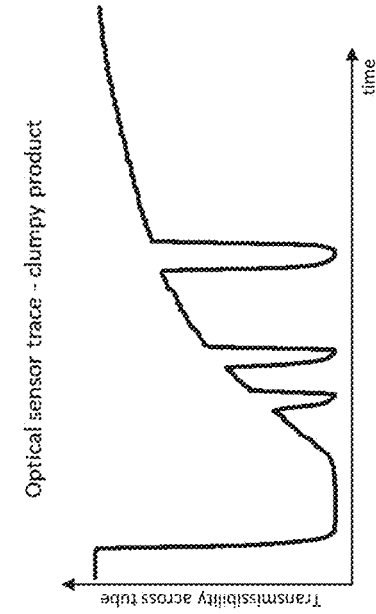
FIG. 2e illustrates a concentrate density trace, showing transmissibility of fluid in the recovery tube over time showing the impact of clumps on the optical density sensor trace.

Some cell products are inclined to aggregate during culture creating "clumps" of material that can accumulate with the normal cell suspension in the separation chamber 40. When the concentrate recovery action occurs, it is common for the clumps to follow behind the fluidized particle bed. This is observed by the density sensor as additional low transmissibility events following the main event as illustrated in FIG. 2e. If these events occur before the controller 10 has determined the target volume has been delivered, the delivery volume can be increased to ensure these materials are not lost to the output material. A user defined setting "Enable Capture Clumps" illustrated in FIG. 2b illustrates the context where such logic can be introduced to the controller 10.

When the trailing edge of the particle suspension concentrate passes the sensor 20, and the threshold settings are within range, controller 10 will record the second density transition to conclude the volume of the concentrate. Through coordination of the pump 30 by the controller 10 the valve assembly 50 will re-direct the fluid flow from Fluid capture path 70 to non-capture path 60 when the concentrate volume has been transferred to the fluid capture path 70 to the captured fluid 75. In this way the captured fluid 75 is representative of the volume of the concentrate observed by the sensor.

If control 10 is at the point to transfer the valve assembly 50 through delivery of the known fluid volume 27 but the density sensor has not detected the first transition, indicating the particle concentrate was not sufficient for the threshold to recognise the first density transition, the control 10 can take alternative actions including deployment of a pre-set minimum volume for captured fluid.

In another control scenario the captured fluid volume can be pre-set for the concentrate recovery event and the concentrate volume detected by the density sensor can be recorded and used to direct a subsequent dilution step to achieve a target captured fluid particle concentration. In another embodiment the dilution step can be integrated into the one particle recovery step by delaying the transition from the fluid capture path 70 to the non-capture path 60 in response to an algorithm managed by the control 10 based on the detected concentrate volume.

It should be appreciated that the fluid will typically be drawn from the concentrate separation chamber 40 in accordance with a laminar fluid flow regime, as is desired for low shear fluid handling to minimise cell damage. However, products flowing through tubing under laminar flow suffer from tube wall boundary layer behaviour that delays fluid at the surface of the tube relative to fluid flowing in the centre of the tube. This results in the "slug" of cell concentrate being drawn out along the tube walls as it progresses causing systematic dilution at the trailing edge. FIGS. 5a and 5b show examples of optical density measurements for slugs of the same volume taken at varying distances along the tube from the slug input to demonstrate the draw out effects on the slug caused by laminar flow, and how it progresses with tube length. As can be observed the density transition 510 indicating the trailing edge of the slug in FIG. 5a is steeper than the corresponding density transition 520 in FIG. 5b. This indicates that the trailing edge of the slug is more drawn out and therefore more diluted from travelling through the longer tube in FIG. 5b.

The ability to observe arrival of the trailing edge relative to the valve assembly allows control over how much of this diluted trailing end of the slug is recovered. For example, in a circumstance where minimum dilution is desired, the second event to shut off the recovery valve may be coordinated to occur before the tailing edge arrives at the valve. In another example, the second event may be coordinated with a selected dilution threshold on the trailing edge, providing a compromise between minimising dilution and maximising particle recovery.

Figure 8:
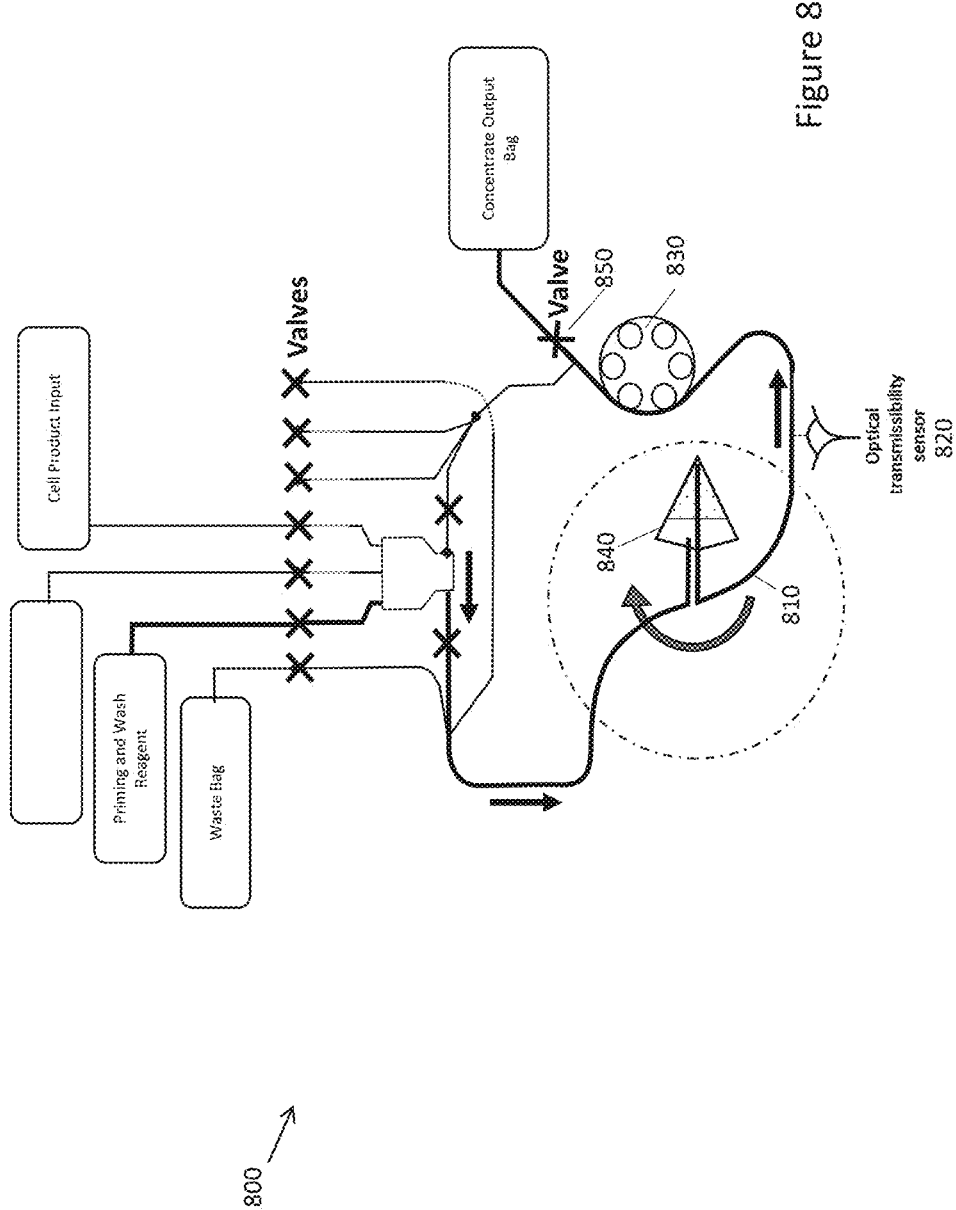
FIG. 8 is a schematic of the fluid recovery system and valve assembly shown in FIGS. 6a-c FIGS. 9a to 9f illustrate an embodiment of a fluid channeling structure formed in the tip of the separation chamber.

Recognition of the systematic losses arising from transit of particle concentrate through process tubing has directed the embodiment design illustrated in FIG. 6a-c and highlighted in FIG. 8 where the path from the concentrating chamber outlet to the valve assembly is aggressively short. It is desirable to have this path as short as possible to reduce potential dilution cause by drawing out of the concentrate.

One embodiment of the control interface is illustrated in FIG. 2b where the thresholds for detecting the start and end of concentrate can be tuned based on recovery goals. The thresholds are based on a baseline sensor reading captured at the start of the flow from the separation chamber before concentrate has reached the sensor. If the recovery goal is to recover the maximum number of cells, the collection start trigger can be set to capture fluid the start of the leading edge, say 90% of the reference reading, and the end trigger at the end of the trailing edge, say 98%. If the recovery goal is to minimise dilution the recovery start trigger may be the end of the leading edge say 30% of the reference reading and end trigger the start of the trailing edge say 50% (cut off before dilution by media fluid at the trailing edge).

It should be appreciated that the relative concentration correlates with the sensed fluid density, in the case of optical density sensors the transmissibility. The collection start and end triggers are based on particle density in the fluid suspension.

The collection start trigger can be a collection threshold density relative to a maximum detected density. In this embodiment the controller is configured to analyse the first density transition to determine the maximum density of the concentrated fluid and determine the first control event for operation of the valve actuator based on the collection threshold density.

Figure 2C:
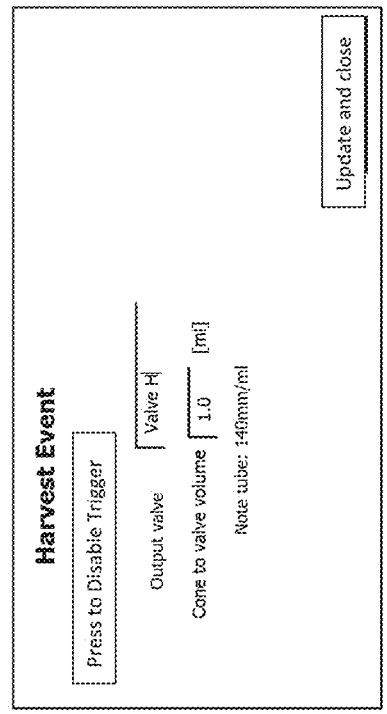
FIG. 2c is an example of a user interface for selecting valve settings that define the volume between the collection chamber and valve assembly for cell collection.

An example of a user interface for setting the start and end collection triggers is shown in FIG. 2b. FIG. 2c shows an example of setting a valve assembly for selecting the valves of a valve assembly to actuate for fluid recovery.

The collection threshold density and dilution threshold density can be selected to minimise dilution of the output product by fluid preceding the concentrate. While the timing of this event can be anticipated by the volumetric distance from the chamber to the sensor, it is important to detect that leading edge since in some circumstances there are so few cells that the control must conclude the optical sensor must be overridden by a volumetric decision. In some use scenarios the collected concentration of cells or particles may be so low that the leading edge of the suspension is difficult or impossible to clearly discern. If so it is desirable to have a mechanism to override the density sensor-based collection. This can be a volumetric trigger based on the fact that at the start of a recovery phase there is a known volume of fluid in the system between the concentrating chamber and the recovery valve assembly. The controller can, in this instance, determine a first control event based on volume of fluid between the concentrating chamber and valve assembly and dynamic fluid volume movement, to cause actuation of the valve actuator to switch to a collection path based on volume in the absence of a density sensor-based collection trigger. The capture cut off may also be a volumetric trigger, to cut off a specified volume after initiating capture. The volume recovery may be set based on anticipated cell recovery and anticipated fluidised bed size based on the concentrating chamber geometry. The volume recovery may be set aiming to minimise dilution while maximising recovery. For example, recovery fluid volume may be between 0.5 to 2 ml, this value may be more or less than this range depending on the embodiment.

The controller uses the pump calibration data to determine when to open and close the output valve actuator in response to the collection triggers. Valve actuation may overlap the transit of the concentrate past the sensor through pre-setting pump position registers when the sensor thresholds are detected. In some embodiments of the invention the pump is a peristaltic pump. The rotary position of the peristaltic pump can be monitored to determine the dynamic fluid volume movement. Controlling the rotary position of the pump allows high precision control over the dynamic fluid movement. The controller can coordinate the pump operation/movement with valve actuation.

This strategy can deliver cell concentrate in a volume down to 0.5 ml with a conservative estimate of 2 ml. The volume of cell concentrate is not required to manage the process. The final delivery volume of the cell concentrate can be increased to a target volume if required. If there are not sufficient cells to trigger the optical density sensor on arrival of the slug, the control detects this failure by understanding the volumetric distance from the chamber to the sensor. The algorithm then defaults to a volumetric delivery strategy.

Embodiments of the fluid recovery system can be used with any system configured to recover concentrated populations of particles suspended in fluid. Embodiments of the fluid recovery system and method can be particularly advantageous in combination with counter flow (also known as reverse flow) centrifuge type concentrator apparatus.

FIG. 3 illustrates the fundamental concepts involved in a counter flow centrifugation process, this will be discussed in the context of a separating a cell population from an input fluid comprising the cells and suspended in the fluid. In a first phase of the process the input fluid with the suspended cells is loaded into the separation chamber 310 and the chamber set spinning around the axis 350, the chamber oriented perpendicularly to the axis such that during rotation the tip of the chamber follows a circular path about the axis, to create the centrifugal acceleration. To counter the centrifugal acceleration fluid 342 is pumped into the chamber for the outermost tip 340, this fluid can be the cell suspension fluid used for initial loading, thereby continuing to introduce cells into the chamber. Alternatively, the chamber 310 may be loaded with a media solution (without any cells in suspension) and the cells introduced after spinning has commenced. The centrifugal acceleration will cause the cells to settle towards the outer end of the chamber 310, by adding the fluid flow 342 in the opposite direction to the direction of settling, the cells can be held suspended. The chamber is shaped so that the local fluid velocity 344 matches the centrifugal acceleration 346 at each radius to create a working zone 345. With the correct flow rate, fluid media and centrifuge speed, cells will accumulate in the working zone 345 and form a stable fluidized bed in that zone. Cells entering the zone will form and join the fluidized bed 345. It should be appreciated that as the cells are introduced to the chamber by the counter fluid flow, these cells will effectively be deposited at the fully settled point as they enter the chamber by the combined action of the fluid flow and centrifugal acceleration, so there is minimal "settling time" using this process.

The fluid is continuously flowing through the chamber 310 with the cells settling from this fluid and accumulating in the fluidised bed so at the inner end of the chamber 330 the fluid should be substantially free of cells an outlet allows this clarified fluid 348 to leave the chamber 310. Once the cells have been accumulated in the fluidised bed a recovery step is used to retrieve the cells as a concentrate where the fluid flow direction 342 is reversed. The fluidised cell bed moves toward the tip 340 of the cone and drawn out of the cone, via the same fluid channel that was used for fluid input. Counter flow centrifugation can also be used to isolate different cell populations by virtue of their response to the conditions in the chamber. Increasing the counter flow rate where a fluidised bed has been formed will result initially in the bed expanding, more intercellular space between each cell, the bed expanding up the cone. Some cells that may be smaller or have "rougher" external topologies may have a different settling velocity resulting in them being unstable in the fluidised bed and being driven out of the cone—inwards. The washing of cells out of the chamber in this way is described as elutriation which is a well known protocol for differential selection of cell populations.

Counter flow centrifugation technology enables a dilute suspension of live cells to be captured into a fluidized bed at concentrations exceeding 1×10⁸ cells per ml. In that state, cells can be processed by diverse strategies that include cell selection by elutriation, media exchange and washing.

The fluid recovery system and method described can be used with a counter flow centrifuge system to provide a cell recovery process that delivers a high concentration of cells as a suspension, rather than a pellet that is created by standard centrifugation.

Figure 4:
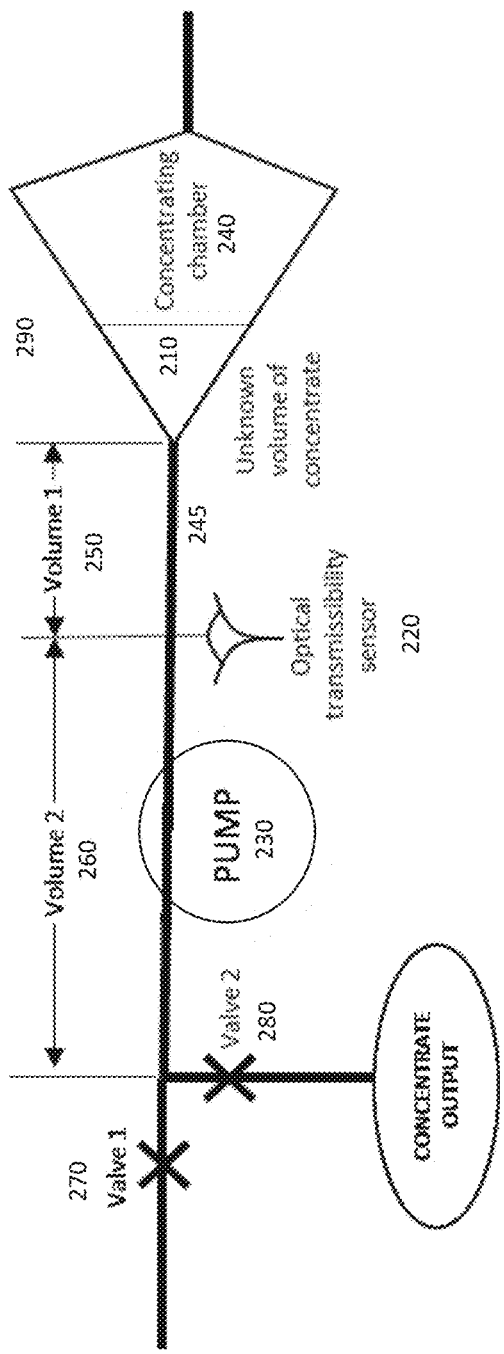
FIG. 4 is a block diagram of an embodiment of a fluid recovery system operatively engaged with a counter flow centrifuge.

FIG. 4 is a block diagram illustrating recovery of the suspension of concentrated particles from a counter flow centrifuge. The block diagram represents the conical concentrating chamber 240 having an unknown volume 210 of fluidised bed of cells in suspension. When the cells are ready for recovery, the pump 230 that creates the counter flow supporting the fluidized bed is reversed, drawing the concentrated cell product out of the cone 240 through the recovery path 245 where it can be re-directed through valves 270 and 280 on the instrument to any target output vessel. It should be appreciated that by virtue of the change in fluid flow direction the suspension of cells forming the fluidised bed will be drawn out of the tip of the cone preceded by fluid substantially free of cells and followed by fluid substantially free of cells. Initially valve 280 will be closed and valve 270 open so that the media fluid is directed to a waste or recycling path. Opening valve 280 and closing valve 270 will cause the fluid to be directed to the capture vessel 290.

Recovery of the fluidized cell bed as a concentrate to an external vessel 290 is initiated by reversing the counter flow pump 230. The fluidized bed is immediately driven to the tip of the cone 240, and ongoing drawing of the fluid from the chamber enables the cells to remain in a fluidized state and be drawn though recovery tube to the recovery valve 280.

The limit to fluidized bed concentration is ultimately avoidance of blocking of the fluid path during the recovery step. The density of the fluidised bed can be adjusted by the counter flow pump before the recovery step enabling optimisation of the suspension concentrate. Counter flow centrifuge processing rate is defined by the centrifuge speed in combination with the counter flow pump rate. The processing rate can be slowed as a coordinated action before the recovery step to minimise risk of cell damage. This coordinated slowing involves controlled slowing of the centrifuge speed and counter flow pump rate so the ratio of pump rate [ml/minute] divided by centrifuge speed in G's is constant. (Note G's being proportional to the square of the centrifuge RPM)

The pump is operated such that fluid is in the laminar flow regime desired for low shear fluid handling, aiming to improve cell survivability. All products flowing through tubing under laminar flow suffer from tube wall boundary layer behaviour that delays fluid at the surface of the tube relative to fluid flowing in the centre of the tube. This results in the "slug" of cell concentrate being drawn out along the tube walls as it progresses. This drawing out effect can be minimized by having the shortest possible distance between the emergence of the "slug" from the separation chamber and the point of delivery to a capture vessel. Embodiments of the instrument and kit design described have been specifically configured to achieve the shortest practical flow distance between the cone tip and the valve specifically located for concentrate recovery.

The controller is configured to monitor the optical density sensor for detection of the leading and trailing edges of the slug. The controller controls the concentrate capture as described above, by triggering actuation of the valves 270, 280 to start recovery and allow fluid flow via a recovery valve 280 to the recovery vessel 290 as the leading edge of the slug approaches the valve 280. And to end recovery based on detection of the trailing edge of the slug by the controller triggering closing the recovery valve as the trailing edge (or a threshold dilution of the trailing edge) passes the recovery valve.

It should be appreciated that for counter flow centrifuges, particles are accumulated in a fluidised bed typically having an unknown volume. However, using this fluid recovery method the volume of recovered concentrate can be calculated by the controller. Embodiments of the controller may be further configured to determine a particle count for the recovered concentrate based on the recovered suspension volume and particle density estimation.

The formulation of a therapeutic product that includes particles is commonly based on creating a controlled concentration of the particles in a combination of media. A formulation step therefore requires determination of the particle count to direct the volume of fluid reagents the particles are to be mixed with. Similar actions are common in processes where reagents interact with particles at other process points, for example such as prior to culture of particles.

The need to understand the particle count in a suspension is therefore a common quality control measurement that is conducted for particle based therapeutic products since it is needed to direct the next steps of the process. Such particle counts are commonly achieved by taking a small sample of the dilute suspension in a total known volume, and an instrument or manual optical methods used to determine the particles in the small sample. The particle count in the total suspension volume is then extrapolated based on the small sample count. The problem is that this sampling and particle counting action requires the primary process to wait until that information has been acquired before proceeding. Further these methods for particle counting are subject to many influences that contribute to variation in the measurement determination, resulting in count variations that range +/−20%. Indirect observation of the entire particle population by the density sensor combined with an accumulation of verification data of the same product and process environment can provide adequate confidence to complete a process without in-process sampling.

In counter flow centrifuge separation processing, the fluidized bed of particles created in the rotating chamber will be characterized by attributes of the particles~nominal external dimension or diameter, bulk density and external surface morphology that affect the stokes settling behaviour in the fluid media supporting the particles. Fluid media attributes include density and viscosity (both sensitive to temperature), and second order characteristics such as thixotropy or shear sensitivity of viscosity. Despite the complexity of these interactions, replication of a process with largely consistent input materials and operating conditions will deliver a consistent fluidized bed behaviour that results in consistent particle density in the fluidised bed when measured as a number of particles per unit volume (particles per ml for example). It should be appreciated that the density of the particles in suspension will be substantially similar between separate batches processed using consistent input materials and operating conditions but the volume of the fluidised may vary significantly between batches reflecting changes in the number of particles.

Embodiments of the fluid recovery process in such instances may include a particle count estimation. In these embodiments the controller is further configured to determine a particle count based on recovered concentrate volume, and particle density estimation for the concentrate based on particle characteristics and operating parameters. The particle density estimation can be based on empirical data, for example historical data from processing previous batches having input materials and operating conditions correlating with the current processing batch. For example, such data may be accumulated externally and input to the controller with the processing procedure data and parameters for the particular process being performed. Alternatively, the controller may be configured to monitor process execution and capture data characterising the particle density (for example density sensor outputs, particle count estimation or verified particle count data) for each executed process. In such embodiments the controller may store such data in a database or other data repository for look-up and comparison with a current processing event to identify one or more correlating previous/historical processing events and look up suspension characteristics to use for particle density estimation.

The recovered concentrate volume can be determined based on the concentrate leading and trailing edge detection and first and second control events. For example, identification of the slug leading edge and trailing edge and the fluid dynamic volume enables the volume of the slug to be determined as illustrated in FIG. 2a. However, the triggers for the first control event and second control events to respectively start and stop collecting fluid can be set at any point relative to the leading and trailing edge of the slug depending on the user defined settings for the cell harvest event. For example, collection may be started as the leading edge of the slug arrives at the collection valve to capture all of the leading edge, but stopped after approximately 50% dilution at the trailing edge of the slug. Based on determining the size of the slug and relative start and stop collection points on the slug, the volume of the suspension can be accurately predicted, and multiplied by the estimated density of the slug to provide a cell count estimation (also referred to as a pseudo cell count). As the recovered volume of particles in suspension can be determined by the controller, the controller can automatically calculate a particle count for the volume using the estimated particle density.

In an embodiment the controller is configured to access a data store of a plurality of historical process information data sets, each data set including particle characteristic data, operating parameter data and an output particle density for the process and identify one or more correlating historical process information data sets for the particle characteristics and operating conditions. The controller can then determine a particle density estimation from the identified historical processing data sets. For example, the particle density estimate may be a looked-up particle density value for the historical processing event having the closest correlation in operating conditions and inputs. In another example the particle density estimate may be calculated as an average of the particle density of a plurality of the closes correlating historical processes.

In another example, historical data may include optical density sensor measurement data and the particle density estimation may be based, at least in part, on comparison between current suspension density data and historical suspension density data. The historical data stored for reference can include data captured during process and verified post processing, for example including actual particle density data verified post processing. It should be appreciated that over time a body of historical data may be accumulated to enable a progressively more accurate estimation method.

In an embodiment each historical data set includes at least a determined particle density and the controller is configured to compare density sensor outputs with identified historical processing data to verify correlation between current processing and identified historical processing data sets. This may also be an optional step used as a validity indicator for correlation between an estimation made based on historical data and actual historic evidence. For example, where an historic record is correlated with a current process based on the processing parameters, inputs and operating conditions, comparison of the optical density characteristics in the historical recorded data and the current measurements may be made. Dissimilarity in the optical characteristics may be indicative of a processing error, or of an incorrect correlation or assumption being used for the particle density estimation, triggering an operator alert for further investigation. Thus, the automated process may be configured for self-verification to some extent.

Embodiments enable automation of particle count estimation based on observation of the particle concentrate suspended in a fluidized bed and measuring the volume of the fluidized bed to estimate the total particle count. The estimate from this action for repeated runs of the process, correlated to external particle counting means can deliver a particle count process capability comparable to that achieved by external counting methods and sufficient for process progression without operator intervention.

Examples of comparable processes can include but are not limited to:
  one batch of input material being processed in a plurality of smaller batches using the same process and operating conditions
  processing of multiple batches where input materials and particles are known to be highly consistent (i.e. low variability in cell size or shape between different individuals, chemical processes generating consistent particle characteristics)

Figure 11:
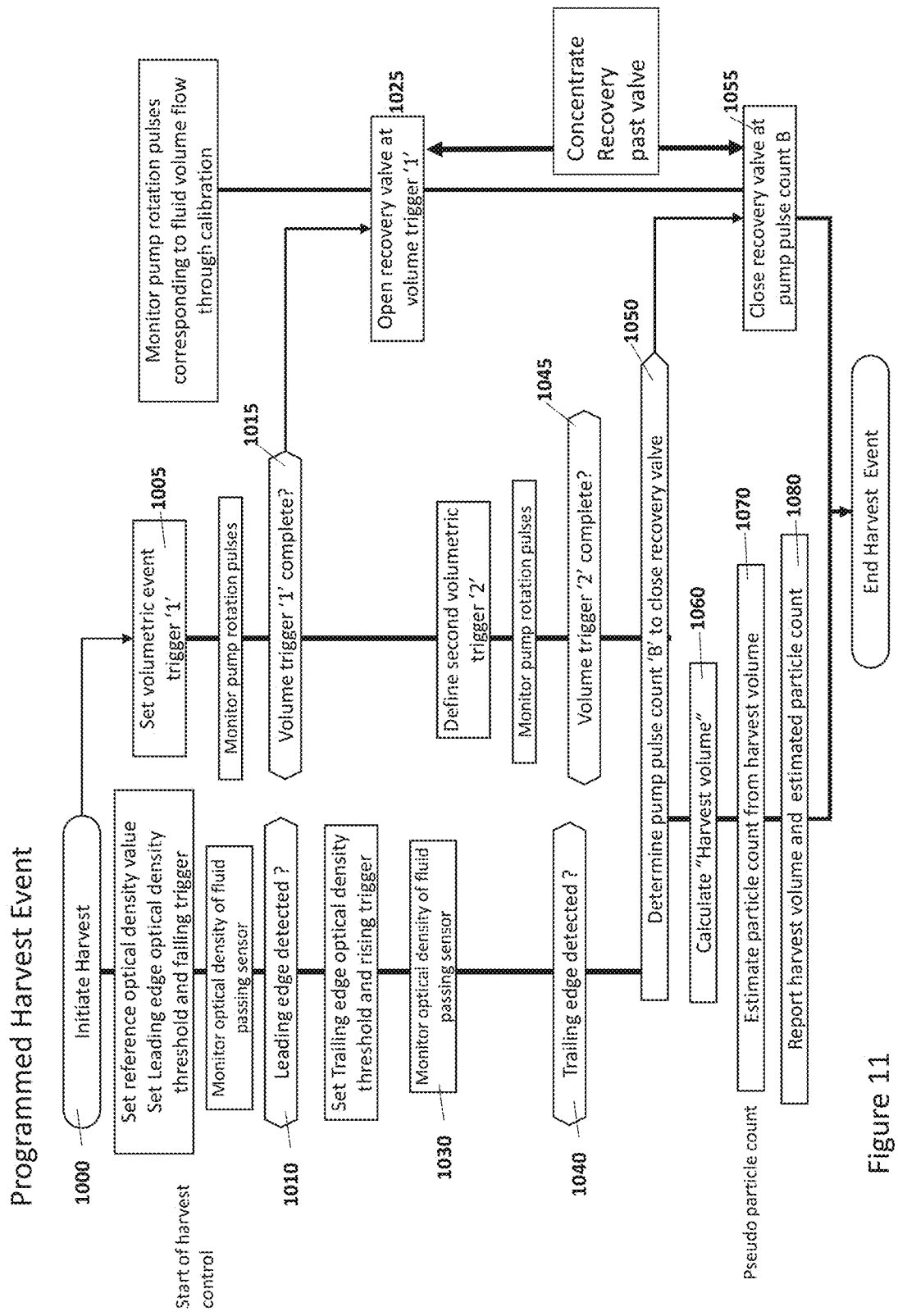
FIG. 11 is a flow chart of the Harvest event directing recovery volume by optical density volume detection with a fall-back volume trigger pre-set.

An example of a counter flow centrifuge particulate (e.g. cell) harvesting event including optional particle count estimation is shown in FIG. 11. After processing to accumulate particles suspended in a fluidised bed within the conical separation chamber, the flow Direction is reversed to initiate harvest 1000. Initiating the harvest can immediately define trigger '1' 1005 that defines when the recovery valve is to open 1025 to switch fluid flow from the recovery tube 48 a fluid capture path 70.

The controller monitors the density sensor to detect the leading edge 1010 of the suspension slug. If the leading edge has not been detected when trigger "1' 1015 occurs, then the control must assume the optical density was too low to trigger the leading edge of the concentrate so a specified volume pre-set will be used. This may be a default system value (for example equivalent to 50% or 75% of the volume of the concentrating chamber) or a user specified value. For example, a user may estimate the anticipated required volume based on previous experience or historical data for the processing being performed.

When the leading edge of the suspension is detected 1010 based on the density sensor output, the controller records the dynamic volume where the leading edge detection occurred, and commences monitoring the optical density sensor to detect the trailing edge of the concentrate 1040.

In parallel to the optical density sensor monitoring, the control will switch the recovery valve 850 at time trigger '1' to cause the fluid from the recovery tube 48 to be directed to a fluid recovery path 70, and appropriate receptacle 75 or further connected processing equipment. The control will continue to deliver concentrate for collection via the recovery valve 850 until the volume determined based on the optical density sensor accumulator has been delivered, or a pre-set volume has been delivered.

When the optical density sensor-based trigger is set the controller continues to monitor the fluid density and fluid volume flow 1030 while fluid is being delivered through the recovery valve if the second density transition event (indicating the trailing edge of the slug) has not yet occurred. When the trailing edge of the slug is detected 1040 the controller determines a recovery valve actuation trigger 1050 to stop recovery 1055. This trigger is based on the trailing edge detection and volume flow. This trigger may be based on a threshold dilution on the trailing edge, and the threshold can be a user controller parameter. The ceasing of recovery may be set based on recovery objectives and trade-offs, for example set of a spectrum for minimal dilution at the cost of some cell recovery to maximising cell recovery at the cost of dilution.

In some embodiments a further volumetric trigger 1045 may also be set to address the event where cell concentration is too low to trigger the leading edge event.

It is also a practical strategy to deliver a controlled volume of concentrate yet record the volume detected by the optical density sensor. The data collected in this way can used to adjust the final delivered volume to a target concentration as a subsequent step for example.

On termination of recovery the volume of the recovered solution is known, further the volume of the concentrated slug captured within the recovery solution may be determined 1060 based on the valve actuation relative to the leading and trailing edges—this determination can take into account dilution by leading and trailing media in accordance with the use programmed recovery parameters. An estimation of the particle count 1070 in the recovered solution can be made as described above, by multiplying the determined recovered suspension volume by a retrieved suspension density estimate, for example retrieved from operator input processing data or looked up suspension density estimation (based on processing parameters and historical data). The system can then output 1080 the total recovered volume, concentration and particle count estimates.

It should be appreciated that the controller may be configured to perform particle count estimation and optionally execute further steps to continue processing. For example, where a target concentration for the output fluid is required the controller may be configured to perform a subsequent dilution step based on the particle count estimate and recovered volume, and calculate a further quantity of fluid to dilute the recovered suspension to a target concentration. This step and calculation of the particle count may occur during recovery. In this example the particle count estimation may be based on detection of leading and trailing edges of the slug, calculation of slug volume. The particle count can be calculated based on the slug volume and historically derived density estimate, and the total volume required for the target concentration determined based on the particle count estimate. The recovery end trigger may then be determined based on the target recovery concentration and set to cut off recovery after a calculated dilution volume of trailing media fluid has also been captured.

Embodiments of the fluid recovery system and methodology can be integrated into concentration apparatus. An example of integrating the fluid recovery system into a counter flow centrifuge will now be discussed with reference to FIGS. 6a-c to 9. An embodiment of a compact counter flow centrifuge system is illustrated in FIG. 6a-c. This system is based on that disclosed in the applicant's co-pending International patent application no. PCT/AU2018/050449 published as WO 2018/204992, claiming priority from Australian provisional patent applications nos. 2017901771 and 2018900193 filed 19 May 2017 and 22 Jan. 2018 respectively, the disclosure of which is incorporated by reference. This system employs a rotary coupling for transfer of the rotating fluid stream to the stationary fluidic system. The central tube of that rotary coupling presents a pathway unencumbered by differential shear. The central fluid path is attached to the dip tube of the conical process chamber. FIG. 6a-c shows an example of an embodiment of a counter flow centrifuge with an embodiment of the fluid recovery system integrated into the device. FIG. 8 is a representative block diagram of the fluid recovery system and valve assembly supported by the embodiment illustrated in FIG. 6a-c. The operation of both these counter flow centrifuge embodiments for cell separation is described in the paragraphs below with reference to FIG. 6a-c.

The compact counter flow centrifuge system 1100 has a reusable subsystem 1200 and a single use replaceable subsystem 1205. The replaceable subsystem comprises disposable components which can be pre-assembled and sterilized for loading thereby simplifying loading protocols. Further pre-assembly can reduce risk of human error. This can also offer low operating costs by reducing the size and complexity of the disposable components compared with current commercial disposable component kits.

The reusable subsystem comprises a rotating motor head 1135, a peristaltic pump 1110 and valve assembly 1120, a casing 1130 houses these system components. The replaceable subsystem comprises a separation chamber 1140, fluid delivery connection 1152 and rotary coupling 1160 connecting the separation chamber 1140 to the fluid connections 1152 and 1154. The single use replaceable subsystem provides a closed environment for execution of counter flow centrifugation processes.

Figure 7:
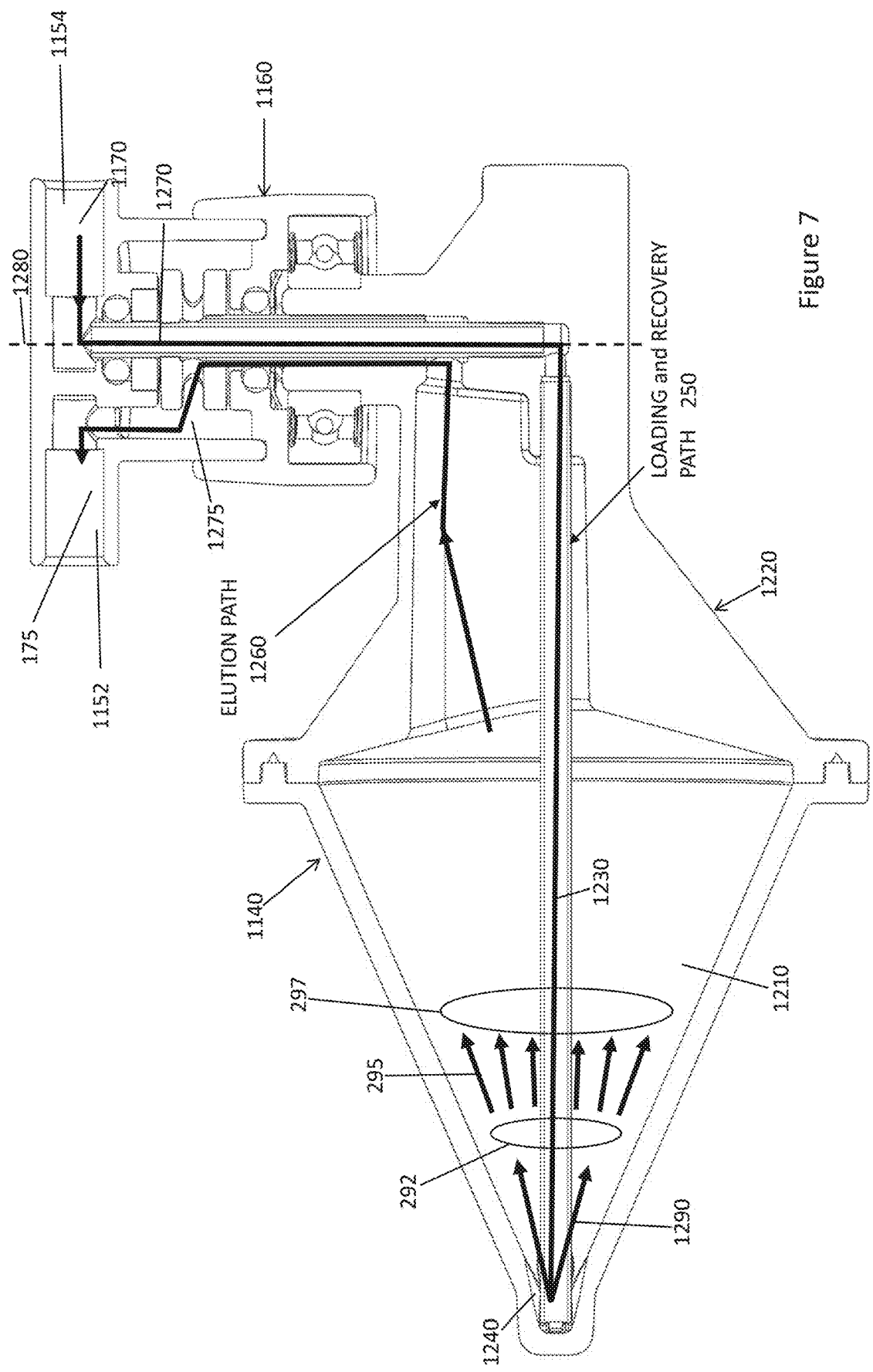
FIG. 7 is an example of a separation chamber apparatus for the centrifuge of FIG. 6a, showing details of the chamber configuration and fluid flow paths for the chamber.

The separation chamber 1140 is configured for low fluid volume and small radius rotation. An example of an embodiment of the separation chamber is illustrated in FIG. 7. The separation chamber 1140 has a substantially conical fluid enclosure portion 1210 connected to a neck portion 1220. A dip tube 1230 extends centrally through the conical fluid enclosure 1210 from the conical tip 1240 through the neck 1220 to provide a fluid path 1250 to the tip of the conical fluid enclosure 1240. The neck portion 1220 also includes an elution fluid path 1260. The neck portion 1220 is connected to the rotary coupling 1160 so the axis of rotation of the chamber is through the neck (reducing the radius of rotation to the length of the chamber). The neck portion is also configured to engage with the rotating motor head 1135 to cause rotation of the separation chamber about the rotational axis. The neck portion configuration to engage with the motor head 1135 can also include a locking mechanism and be counter weighted to balance the separation chamber.

The fluid delivery manifold 1150 comprises a first fluid port 1170 and a second fluid port 1175 configured for fluid communication with the separation chamber 1140, and a plurality of fluid paths configured for connection to external fluid supply components 1180 for delivery of fluid to or from the first fluid port 1170 and the second fluid port 1175. At least one of the fluid paths is configured for engagement with the valve assembly 1120 for selective opening or closing by operation of the valve assembly. The manifold also includes a pump engagement portion 1190 configured to enable operable engagement between the peristaltic pump 1110 and fluid paths 1180 to cause fluid flow within the manifold 1150 by operation of the peristaltic pump 1110.

In FIG. 7 a rotary coupling 1160 connects the separation chamber 1140 to the fluid delivery manifold connections 1152 and 1154. The rotary coupling is configured to allow rotation of the separation chamber 1140 about a rotational axis relative to the fluid delivery manifold 1150 while the fluid delivery manifold is held in a fixed position by the case 1130. As the rotary coupling is connected to the neck of the chamber the rotational axis for the chamber is through the neck of the chamber—so the radius of rotation is only the length of the chamber from the axis to the exterior end of the chamber tip. The rotary coupling 1160 also provides a first fluid communication path 1270 between the dip tube 1230 and the first fluid port 1170 and a second fluid communication path 1275 between the elution fluid path 1260 and the second fluid port 1175. These fluid communication paths are formed in the rotary coupling.

An advantage of the system is that the same system components and processing functionality can be utilized in a laboratory type setup as for a fully scaled commercial production system. The configuration of the separation chamber enables the small rotational radius and high rotation speed. An example of the separation chamber is shown in FIG. 7, the separation chamber 1140 comprises a substantially conical fluid enclosure 1210 and a neck portion 1220. It should be appreciated that although the embodiment shown used a conical fluid enclosure, embodiments may not always use a perfect cone, some variation on this structure is contemplated within the scope of the present invention, for example a short straight sided portion may be used near wide end of the cone or at the tip, alternatively a stepped conical structure may be used. A dip tube 1230 extends through the fluid enclosure 1210 from the neck for delivery of fluid to the tip of the cone 1240. An elution path 1260 is provided through the neck 1220. It should be appreciated that by using an internal dip tube 1230 is a significant divergence from commercial counter flow centrifugation architecture, which provides a fluid path external to the separation chamber and the separation chamber has an inlet at the tip to supply the counter fluid flow to the separation chamber.

The process experienced by cells within the spinning cone 1210 of this small device is identical to the process within larger implementations of counter flow centrifugation. Fluid 1290 entering at the tip of the cone 1240 causes a counter flow to the centrifugal acceleration causing cells to accumulate in a fluidised bed that progressively builds from the tip of the cone. When a dilute suspension of cells is presented to the processing chamber 1210, at the right conditions, the cells will be trapped in the chamber 1210 as a fluidized bed that progressively builds from the tip of the cone. The media that was carrying the cells progresses to the inner, larger diameter of the cone and exits via a fluid path co-axial to the central supply and through the rotary coupling.

The cells trapped in the chamber form a fluidized bed, where the cells are separated from each other by the process fluid. The density of the bed can be adjusted by changing the counter flow fluid flow rate or the centrifuge speed. This increases or decreases the cell concentration (cells/ml) in the bed. A conservative concentration of $1\times10^8$ can be reliably managed and cells in the 2 to 5 micron size range can be comfortably processed at 2× to 4× these concentrations within the bed.

Recovery of the fluidized cell bed as a concentrate to an external vessel is initiated by reversing the counter flow pump. The fluidized bed is immediately driven to the tip of the cone, ongoing drawing of the fluid from the chamber enables the cells to remain in a fluidized state. The fluidized bed travels through the central fluid line of the rotary coupling and emerges as a "slug" of concentrated cells.

The separation chamber design shown in FIG. 7 uses an internal straw (also referred to as a dip tube) for the fluid connection to the tip of the cone. This delivers a range of significant benefits:

No external fluid connection to the high-pressure region of the cone eliminating manufacturing and handling risks associated with the external plumbing configuration.

The fluid flow pattern of cell suspensions entering the fluid chamber is not influenced by geometry of the external plumbing that is required to turn back on itself to align to the conical chamber geometry.

External fluid lines and associated u-bends results in the highest centrifugal zone occurring outside the separation chamber. Heavy particulates and cell aggregates accumulate in the highest centrifugal zone. In known commercial systems this highest centrifugal zone occurs outside the separation chamber, for example in a bend in external plumbing near the fluid input at the tip of the separation chamber. In embodiments of the present invention this critical highest centrifugal zone is within the tip of the cone. Where the cone is transparent this highest centrifugal zone can also be clearly observed for managed intervention.

The central dip tube in the cone can be created from hypodermic tubing that is technically precise, approved for medicinal product contact and manufactured in sufficient volume to be low in cost. Hypodermic tubing is also a well-known component of the hazardous waste stream for these products after use. This can have advantages both for initial production cost and waste disposal costs for the separation chamber component.

The dip tube design in combination with features in the cone moulding can create well controlled reproducible fluid flow geometry in the fluid chamber. For example, using an interference fit between the dip tube and the chassis components, the tube cut length, moulding features and assembly tolerances are eliminated by axial re-positioning of the tube through the virtue of the interference fit. An embodiment of a fluid channeling structure formed in the tip of the separation chamber is illustrated in FIGS. 9a to 9f, the tip 400 of the conical fluid enclosure includes a channeling structure with a central portion 420 for receiving the fluid output from the dip tube 410 and lobes 430 spaced around the central portion to disperse the fluid flow around the conical fluid enclosure. The fluid channeling structure can also be configured to assist in locating and supporting the dip tube 410. For example, as shown in FIGS. 9b and 9f, the central portion 420 is sized to receive the end of the dip tube 410, which can be held in place by the centrifugal force (shown in FIGS. 9c and 9f). In this embodiment the central portion 420 includes ledges 440 between the lobes 430 to control the dip tube axial location and ensure a consistent open fluid communication pathway between the dip tube 410 and the fluid chamber. Fluid from the dip tube enters the central portion 420 and flows out via the lobes 430 which provide the opening to the fluid enclosure. The embodiment shown uses three lobes evenly spaced around the tip, however, other structures may be use, for example, 4 or more lobes, or a plurality of evenly spaced radial channels. It should be appreciated that such a structure may simplify device manufacturing and assembly, in particular by reducing the precision required during the assembly process to ensure correct placement of the dip tube 410.

Fluid can be recovered from the chamber by reversing the fluid flow to draw the fluidised bed (i.e. concentrated cells) out through the dip tube 410. It should be appreciated that it is desirable to draw the fluidised bed out of the cone with minimal disturbance to the media environment the cells are suspended in, and minimising dilution during the recovery process. The process conditions within the bed are controlled by centrifuge speed and fluid flow rate. Similar fluidised bed conditions can be created at a range of speeds by matching the flow rate. This allows the centrifuge rotation speed and fluid flow rate to be slowed as a coordinated action (for example controlled by the microprocessor controller) retaining the fluidised bed in a stable condition but at a slower process rate creating more favourable conditions for the recovery process. Slowing centrifugal rotation and flow rate may also reduce risk of cell damage during the recovery process. To maximise concentrated fluid recovery, it is also desirable to have a very small gap between the dip tube and the end of the cone tip to reduce the amount of cell free fluid that may be drawn into the dip tube with the last of the fluidised bed, and reduce dilution towards the end of the fluidised bed recovery.

Figure 9:
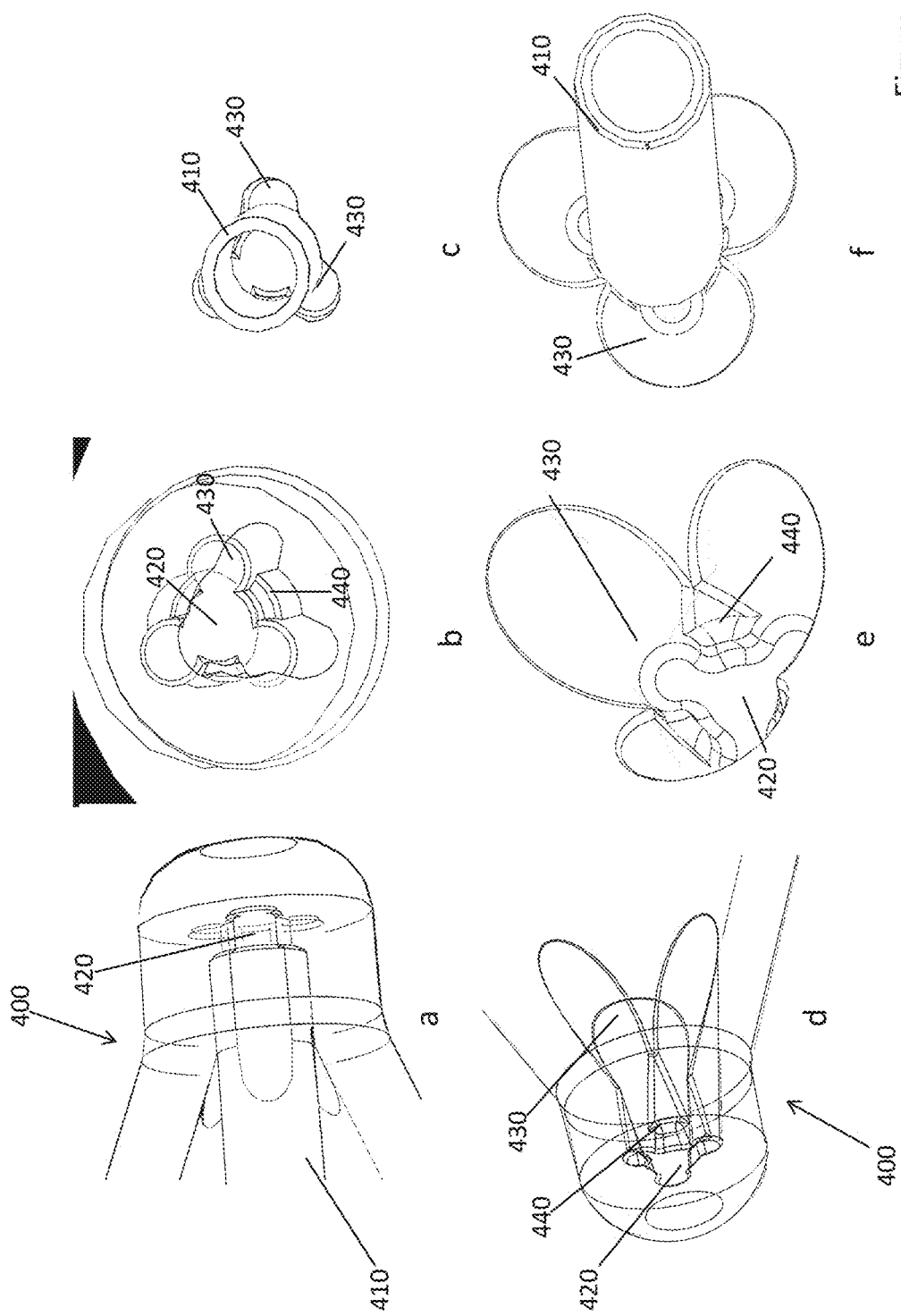

The structure of the cone tip 400 can be designed to minimise the gap for good recovery outcomes. It should be appreciated that the channeling structure for supporting the dip tube as shown in FIG. 9 can be advantageous as the supporting ledge 440 and lobe 430 structure reduces the access area around the dip tube entrance for cell free liquid behind the fluidised bed. The central portion should be fully occupied by the fluid of the fluidised bed until the last moments of the fluidised bed being drawn out of the tube. Provided the flow rate is controlled to maintain stability of the fluidised bed the lobes should funnel all of the concentrated fluid to the dip tube ahead of the trailing cell free fluid to minimise dilution.

As described above with reference to FIGS. 5a and 5b the travel distance for the slug between the separation chamber and recovery point affects the amount of dilution of the slug, particularly at the trailing edge. This is exacerbated by the laminar flow regimes used to minimise cell damage during processing and recovery. All products flowing through tubing under laminar flow suffer from tube wall boundary layer behaviour that delays fluid at the surface of the tube relative to fluid flowing in the centre of the tube. This results in the "slug" of cell concrete being drawn out along the tube walls as it progresses. This can only be minimized by having the shortest possible distance between the emergence of the "slug" and the point of delivery. In this embodiment the instrument and kit design has been specifically configured to achieve the shortest practical flow distance between the cone tip and the valve 850 specifically located for concentrate recovery.

In the embodiment illustrated in FIGS. 6a-c and FIG. 8 the device 800 is configured to minimise the recovery path 810 length. In particular, arranging the system components to reduce the length of tubing required to connect the fluid recovery path from the chamber 840 to the output, via the optical density sensor 820, pump 830 and output valve 850. It should be appreciated that although the recovery path tubing is a component of the disposable/consumable kit for this instrument the fixed configuration of the system components means that the recovery tube length is fixed and therefore the volume between the density sensor 820 and outlet valve 850 is known. Embodiments where the consumable kit is provided as a preformed manifold can also have advantages in minimising potential variation due to manufacturing tolerance or human installation.

Before starting a recovery phase when the pump is reversed for fluid recovery, there is a volume of fluid between the tip of the cone and the outlet valve that contains no cells. This volume is very consistent as it is defined by the kit manufacture, so the instrument can anticipate when to open the valve just as the concentrate "slug" approaches. This feature and close monitoring of pump position by the control system allows a controlled final delivery volume past the output valve to be consistent, for example within +/−0.2 ml.

Another consideration is to understand that the conical process chamber 840 is unlikely to be comprehensively full of cells. Different protocols and batches will result in different cell populations that when concentrated at a given counter flow condition will fill the chamber to different levels.

It is common for live cell protocols to seek a target cell concentration (cells/ml) in the output product. When cells are rare and precious it is particularly important to recover the cells you have in the smallest practical volume to enable dilution to the target final formulation volume rather than additional concentration steps.

To address this issue, the instrument includes an optical density sensor 820 across the recovery fluid path 810. This sensor observes the transmissibility of light through the single use tubing 810. When the cell concentrate "slug" initially moves past the sensor 820 the transmissibility drops low. While the timing of this event can be anticipated by the volumetric distance from the chamber to the sensor, it is important to detect that leading edge to maximise the accuracy of recovery outcomes. It should also be appreciated that in some circumstances there are so few cells that the control must conclude the optical sensor must be overridden by a volumetric decision.

As the last of the concentrate slug moves from the chamber past the sensor there is a recovery of the transmissibility observed by the sensor proportional to the reducing cell concentration in front of it. By setting a threshold on the transmissibility recovery to 95% for example, the bulk of the cell population will have passed the sensor. This trigger is then used by the control to define the volume that is directed past the output valve.

The recovery control processing is integrated into the system controller, to trigger recovery valve actuation and control the pump is performed in accordance with the process described above.

The system controller can be configured to detect the first density transition and record the leading edge of the concentrated fluid at the sensor. The system controller can be configured to detect the second density transition record the second density transition and determine the volume of concentrate for recovery, this can be based on a % dilution threshold on the trailing edge of the concentrated fluid. The system controller can be configured to use pump calibration data to determine when to open and close the output valve 850 actuator in response to the sensor trigger and determined volume. Valve actuation may overlap the transit of the concentrate past the sensor.

The controller can also be configured to monitor a volumetric trigger for a recovery event, wherein at the time fluid recovery is initiated a volume of fluid in the recovery between the concentrating chamber and the valve assembly is determined and a recovery control event override trigger is set to trigger operation of the valve actuator based on the dynamic fluid volume movement, in the absence of detecting a first density transition.

In some embodiments the system controller may be configured to execute more than one fluid recovery event. For example, if the centrifuge is used for separation of different fluid layers as part of a density gradient separation protocol. Density gradient separate cell populations (i.e. based on differing size and mass density), to populate different layers of a fluid with carefully controlled density and viscosity. A recovery event may be triggered to selectively recover each of the fluid layers and associated cell populations to different output paths. For example, in such an embodiment the valve assembly may be configured to switch a single incoming fluid path selectively to a non-recovery path or one of two separate recovery paths. This switching to a first recovery path being triggered based on detection of a first slug, and switching to the second recovery path based on detection of different optical densities, so the second density transition will be indicative of a transition between the two cell populations and collection triggered accordingly to switch between the first and second collection paths. It should be appreciated that such a technique may also be used for recovery of different portions of a slug for a single population. For example, a first recovery path may be used for capturing the suspension at maximum concentration (the section between the leading and trailing edges) and a second recovery path used for capturing the somewhat diluted leading and/or trailing edge sections of the suspension.

Returning the counter flow centrifuge into the cell capture direction in recirculation mode enables recovery of any cells that were not captured by this strategy for process verification purposes or to form the beginning of the next cell capture process step.

This strategy can deliver cell concentrate in a volume down to 0.5 ml with a conservative estimate of 2 ml. It should be appreciated that an advantage of this fluid recovery system and method is that the volume of cell concentrate is not required to manage the process. Thus, cells may be recovered at the maximum practicable concentration, without prior knowledge of the actual cell population. The final delivery volume of the cell concentrate can be increased to a target volume if required. It is preferred for cell therapies to dilute recovered populations rather than require further concentration steps, as concentration processes are typically more likely (than dilution) to cause cell damage or death.

In embodiments of the system if there are not sufficient cells to trigger the optical density sensor on arrival of the slug, the control detects this failure when a leading edge trigger has not been observed when the valves are being changed under volume control to the delivery settings. The controller recovery algorithm can then default to a volumetric delivery strategy.

Figure 10:
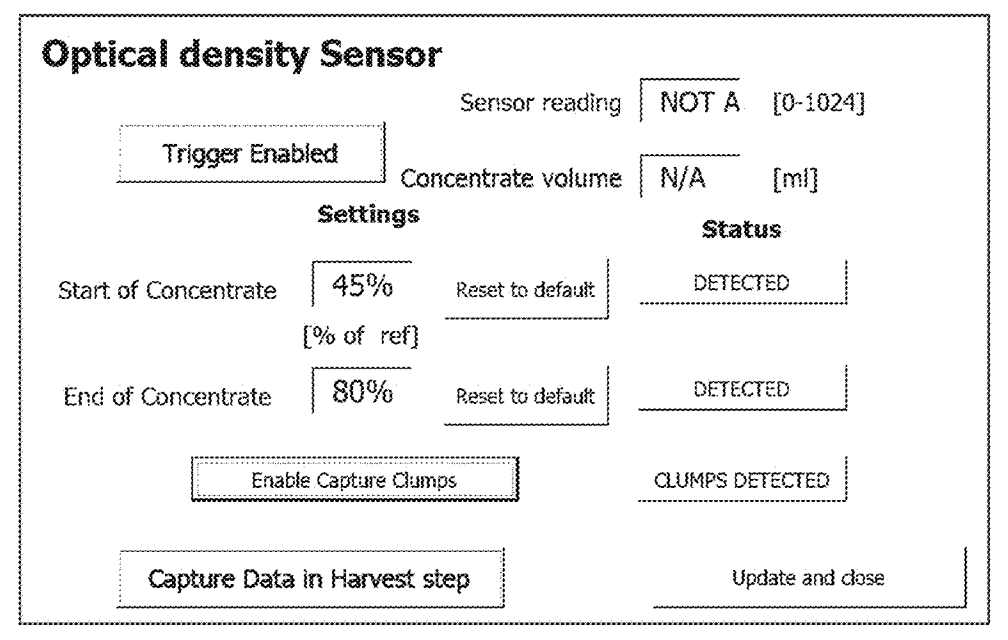

FIG. 10 shows an example of a user interface for setting trigger conditions for leading and trailing edge detection by the optical sensor. It should be appreciated that this may vary between embodiments. A first consideration for the optical density sensor is to determine and maintain a baseline reference for the tube carrying fluid media. This may be obtained by optical sensor monitoring during an initial setup phase with only media fluid in the tubing. The controller may be configured to execute a density sensor initialisation process as part of the system initialisation with the objective of minimising run time for LED stabilisation, determination of an initial baseline density reference–characterising the tube and fluid media optical characteristics. This baseline can be utilised for background monitoring of the optical density sensor to detect drift and avoid compromising trigger detection settings. Background activity executed for each optical density sensor sample can include recognition of tube full of fluid or dry (including bubbles) based on defined settings, contributing to long term averaging of full tube characteristics. The sampling rate for the density sensor may be varied based on processing phases. For example, during separation chamber loading and separation phases a lower sampling rate may be used compared to during a recovery phase. If monitoring for bubbles in the media fluid a higher sampling rate may also be used.

During fluid recovery the sample rate for the optical sensor may be increased, to improve accuracy of slug detection and recovery triggering. For example, during trigger enabled steps increase monitoring rate to 10 msec. The presence of the slug can be differentiated by the controller from a bubble detection response as the slug will typically cause a sustained change in density. The controller is configured to analyse the optical sensor output to recognise the return to transmissibility indicating the trailing edge of the slug. Slug detection may trigger an increase in sample rate to improve accuracy of trailing edge detection and transmissibility recovery monitoring to determine the recovery end trigger.

It will be understood to persons skilled in the art of the invention that many modifications may be made without departing from the spirit and scope of the invention.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or any other country.

The invention claimed is:

1. A fluid recovery system configured to operatively engage with a concentrator apparatus comprising a concentrating chamber having a first fluid path and a second fluid path connected in line with a fluid pumping mechanism, whereby to recover concentrated fluid from the concentrating chamber fluid enters the concentrating chamber via the first fluid path as fluid exits the concentrating chamber via the second fluid path to a fluid recovery tube, and a recovery valve assembly and a valve actuator configured to switch flow of fluid from the fluid recovery tube to one of two or more fluid output tubes, at least one fluid output tube providing a fluid capture path and at least one fluid output tube providing a non-capture path;

the fluid recovery system comprising:
a density sensor configured to detect density of fluid in the fluid recovery tube preceding the recovery valve assembly when operatively engaged with the concentrator apparatus; and
a controller configured to:
monitor operation of the fluid pumping mechanism to determine dynamic fluid volume movement of fluid in the fluid recovery tube,
monitor the density sensor to identify:
a first density transition in fluid in the fluid recovery tube from a first density to a second density, the second density being higher than the first density, the density transition being indicative of a leading edge of a portion of concentrated particles in the fluid passing through the recovery tube; and a second density transition from the second density to a third density, the third density being lower than the second density, the density transition being indicative of a trailing edge of a portion of concentrated particles in the fluid passing through the recovery tube;

and determine based on a fluidic volume between an outlet of the concentrating chamber and recovery valve assembly a first control event for switching fluid flow in the fluid recovery tube to the fluid capture path;

determine, based on detection of the first density transition, the second density transition and dynamic fluid volume movement, a volume of suspension containing target material for recovery, determine a second control event for switching fluid flow in the fluid recovery tube from the fluid capture path to the non-capture path to capture the volume of suspension containing target material for recovery; and control operation of the valve actuator in accordance with the first control event to switch between the non-capture path and the fluid capture path, and in accordance with the second control event to switch fluid flow between the fluid capture path and the non-capture path.

2. A fluid recovery system as claimed in claim 1 wherein the controller is further configured to operate the fluid pumping mechanism to control the dynamic fluid volume movement.

3. A fluid recovery system as claimed in claim 1 wherein the fluid pumping mechanism is a peristaltic pump and the controller is configured to monitor the dynamic fluid volume movement based on and monitoring rotary position of the peristaltic pump and/or calibration of a pump tube of the peristaltic pump.

4. A fluid recovery system as claimed in claim 3 where detection of the first density transition representing a concentrate leading edge threshold density is relative to a reference density determined at the start of the recovery event, before a concentrate can be observed by the sensor.

5. A fluid recovery system as claimed in claim 4 wherein a concentrate volume start trigger is initialised by recognition of a maximum density of the concentrate in the fluid, the controller is configured to analyse the first density transition to determine the dynamic fluid volume where the maximum density of the concentrate occurs and determine the first control event for operation of the valve actuator to align with arrival of the maximum density of the concentrate at the recovery valve assembly.

6. A fluid recovery system as claimed in claim 4 wherein the controller is configured to override a density-based volume determination when additional clumps of concentrated particles are observed, to extend a target recovery volume until all target material is recovered.

7. A fluid recovery system as claimed in claim 4 wherein a collection stop trigger is a dilution threshold density relative to a maximum detected density and the controller is configured to analyse the second density transition to determine the second control event for operation of the valve actuator based on the dilution threshold density.

8. A fluid recovery system as claimed in claim 1 wherein the controller is further configured to determine a particle count for a current process based on a recovered concentrate volume, and a particle density estimation for the concentrate for the current process based on particle characteristics and operating parameters.

9. A fluid recovery system as claimed in claim 8 wherein the controller is configured to:

access a data store of a plurality of historical process information data sets, each data set including particle characteristic data, operating parameter data and an output particle density for a historical process;

identify one or more correlating historical process information data sets for the current process based on particle characteristics and operating conditions; and determine a particle density estimation for the current process from the identified historical process information data sets.

10. A fluid recovery system as claimed in claim 9 wherein each one of the plurality of historical process information data set includes at least a determined particle density for the historical process and the controller is configured to compare the output particle density for the current process with each one of the identified one or more correlating historical process information data sets to verify correlation between current processing and each one of the identified correlating historical process information data sets.

11. A fluid recovery system as claimed in claim 1 wherein the controller is further configured to determine a first control event based on volume of fluid between the concentrating chamber and the valve assembly, and dynamic fluid volume movement, to cause actuation of the valve actuator to switch to the fluid capture path based on volume in the absence of a density sensor-based collection trigger.

12. A fluid recovery system as claimed in claim 11 wherein the controller is further configured to determine the second control event based on a specified volume in the absence of a density sensor-based collection trigger.

13. A concentrator apparatus comprising:

a fluid pumping mechanism;

a concentrating chamber having a first fluid path and a second fluid path connected in line with the pumping mechanism to introduce fluid to the concentrating chamber, whereby to recover concentrated fluid from the concentrating chamber fluid enters the concentrating chamber via the first fluid path as fluid exits the concentrating chamber via the second fluid path;

a fluid recovery tube connected to the second fluid path of the concentrating chamber;

a recovery valve assembly and a valve actuator configured to switch flow of fluid from the fluid recovery tube to one of two or more fluid output tubes, at least one fluid output tube providing a fluid capture path and at least one fluid output tube providing a non-capture path;

a density sensor configured to detect density of fluid in the recovery tube preceding the recovery valve assembly when operatively engaged with the concentrator apparatus; and a controller configured to:

control operation of the fluid pumping mechanism to control dynamic fluid volume movement of fluid in the fluid recovery tube, monitor the density sensor to identify:

a first density transition in fluid in the fluid recovery tube from a first density to a second density, the second density being higher than the first density, the density transition being indicative of a leading edge of a portion of concentrated particles in the fluid passing through the recovery tube; and a second density transition from the second density to a third density, the third density being lower than the second density, the density transition being indicative of a trailing edge of a portion of concentrated particles in the fluid passing through the recovery tube; and determine based on a fluidic volume between an outlet of the concentrating chamber and recovery valve assembly a first control event for switching fluid flow in the fluid recovery tube to the fluid capture path;

determine based on detection of the first density transition, the second density transition and dynamic fluid volume movement, a volume of suspension containing target material for recovery;

determine a second control event for switching fluid flow in the fluid recovery tube from the fluid capture path to the non-capture path to capture the volume of suspension continuing target material for recovery; and control operation of the valve actuator in accordance with the first control event to switch between the non-capture path and the fluid capture path, and in accordance with the second control event to switch fluid flow between the fluid capture path and the non-capture path.

14. A concentrator apparatus as claimed in claim 13 wherein the concentrator apparatus is a counter flow centrifuge and the controller is further configured to control concentrating chamber rotation and the pumping mechanism to:

during a concentrating operation phase cause fluid flow in a counter flow direction to cause fluid to enter concentrating chamber via the second fluid path whereby centrifugal force due to rotation of the concentrating chamber and the counter fluid flow cause concentration of particles in the fluid into a fluidised bed to provide the concentrated fluid, and during a recovery operation phase cause fluid flow in a recovery direction to cause fluid to enter the chamber via the first fluid path as fluid is drawn from the concentrating chamber via the second fluid path, whereby the fluid flow and centrifugal force due to rotation of the concentrating chamber cause the fluidised bed of concentrated fluid to move to the second fluid path and be drawn from the concentrating chamber through the fluid recovery tube.

15. A concentrator apparatus as claimed in claim 14 wherein the controller is configured to slow operation of the pumping mechanism and chamber rotation sustaining the stability of the fluidised bed counter flow conditions prior to the recovery operation phase.

16. A concentrator apparatus as claimed in claim 15 wherein the counter flow centrifuge is a compact counter flow centrifuge system comprising:

a reusable subsystem; and a single use, replaceable subsystem, the reusable subsystem comprising:

a rotating motor head;

the fluid pumping mechanism in a form of a peristaltic pump;

a concentrator valve assembly; and a case housing the rotating motor head, peristaltic pump, and concentrator valve assembly, and the single use, replaceable subsystem comprising:

a concentrating chamber configured for low fluid volume and small radius rotation, comprising a substantially conical fluid enclosure portion connected to a neck portion, and having a dip tube extending centrally through the conical fluid enclosure from a conical tip through the neck to provide a fluid path to the tip of the conical fluid enclosure, the neck portion further comprising an elution fluid path;

a fluid delivery manifold comprising a first fluid port and a second fluid port configured for fluid communication with the concentrating chamber, a plurality of fluid paths configured for connection to external fluid supply components for delivery of fluid to or from the first fluid port and the second fluid port at least one of the fluid paths being configured for engagement with the concentrator valve assembly whereby fluid paths can be selectively opened or closed by operation of the concentrator valve assembly, and a pump engagement portion configured to enable operable engagement between the peristaltic pump and fluid paths to cause fluid flow within the manifold by operation of the peristaltic pump; and a rotary coupling connecting the neck portion of the concentrating chamber to the fluid delivery manifold and providing a first fluid communication path between the dip tube and the first fluid port and a second fluid communication path between the elution fluid path and the second fluid port, the rotary coupling being configured to allow rotation of the concentrating chamber about a rotational axis through the neck relative to the fluid delivery manifold while the fluid delivery manifold is held in a fixed position by the case;

the neck portion being further configured to engage with the rotating motor head to cause rotation of the concentrating chamber about the rotational axis, the single use replaceable subsystem providing a closed environment for execution of counter flow centrifugation processes.

17. A concentrator apparatus as claimed in claim 16 wherein the pump, density sensor and valve assembly are arranged to provide a short fluid path length for a recovery path from the concentrating chamber through the manifold past the density sensor and the pump engagement portion to an output.

18. A concentrator apparatus as claimed in claim 16 wherein the controller is configured to monitor the dynamic fluid volume movement based on and monitoring rotary position of the peristaltic pump and/or calibration of a pump tube of the peristaltic pump.

19. A concentrated fluid recovery method implemented in a fluid recovery system of a concentrator apparatus comprising a fluid pumping mechanism, a concentrating chamber having a first fluid path and a second fluid path connected in line with the pumping mechanism, whereby to recover concentrated fluid from the concentrating chamber fluid enters the concentrating chamber via the first fluid path as fluid exits the concentrating chamber via the second fluid path to a fluid recovery tube, and a recovery valve assembly and a valve actuator configured to switch flow of fluid from the fluid recovery tube to one of two or more fluid output tubes, at least one fluid output tube providing a fluid capture path and at least one fluid output tube providing a non-capture path; a density sensor configured to be positioned to detect density of fluid in the recovery tube a fixed distance along the fluid recovery tube preceding the recovery valve assembly, when operatively engaged with the concentrator apparatus; and a controller;

the method comprising steps of:

monitoring by the controller operation of the fluid pumping mechanism to determine dynamic fluid volume movement of fluid in the fluid recovery tube, monitoring density of fluid flowing in the recovery tube by the controller using the density sensor;

identifying a first density transition in fluid in the fluid recovery tube from a first density to a second density, the second density being higher than the first density, the density transition being indicative of a leading edge of a portion of concentrated particles in the fluid passing through the recovery tube;

determining by the controller based on detection of the first density transition, dynamic fluid volume movement, and a fluidic volume between an outlet of the concentrating chamber and recovery valve assembly a first control event for switching fluid flow in the fluid recovery tube to the fluid capture path;

identifying a second density transition from the second density to a third density, the third density being lower than the second density, the density transition being indicative of a trailing edge of a portion of concentrated particles in the fluid passing through the recovery tube;

determining, based on detection of the second density transition and dynamic fluid volume movement, a volume of suspension containing target material for recovery;

determining a second control event for switching fluid flow in the fluid recovery tube from the fluid capture path to the non-capture path to capture the volume of suspension containing target material for recovery; and controlling operation of the valve actuator in accordance with the first control event to switch between the non-capture path and the fluid capture path, and controlling operation of the valve actuator in accordance with the second control event to switch fluid flow between the fluid capture path and the non-capture path.

20. The method as claimed in claim 19 wherein determining the first control event for operation of the valve actuator is based on a calculated volume preceding a collection start trigger relative to the leading edge of the concentrated fluid and the volume of fluid in the recovery tube between the density sensor and valve assembly.

21. The method as claimed in claim 19 wherein the concentrator apparatus is a counter flow centrifuge, the method further comprising the step of slowing operation of the fluid pumping mechanism and chamber rotation sustaining stability of fluidised bed counter flow conditions prior to a recovery operation phase.

\* \* \* \* \*